(12) United States Patent
Hermel-Davidock et al.

(10) Patent No.: US 10,336,852 B2
(45) Date of Patent: *Jul. 2, 2019

(54) AMPHIPHILIC GRAFT COPOLYMERS

(71) Applicants: Becton, Dickinson and Company, Franklin Lakes, NJ (US); The University of Massachusetts, Amherst, MA (US)

(72) Inventors: Theresa Hermel-Davidock, Newton, NJ (US); Edward Bryan Coughlin, Amherst, MA (US)

(73) Assignees: Becton, Dickinson and Company, Franklin Lakes, NJ (US); The University of Massachusetts, Amherst, MA (US)

(*) Notice: Subject to any disclaimer, the term of this patent is extended or adjusted under 35 U.S.C. 154(b) by 55 days.

This patent is subject to a terminal disclaimer.

(21) Appl. No.: 15/484,593

(22) Filed: Apr. 11, 2017

(65) Prior Publication Data

US 2017/0233517 A1    Aug. 17, 2017

Related U.S. Application Data

(60) Continuation of application No. 14/834,638, filed on Aug. 25, 2015, now Pat. No. 9,714,309, which is a
(Continued)

(51) Int. Cl.
*C08F 255/02* (2006.01)
*C08F 8/00* (2006.01)
(Continued)

(52) U.S. Cl.
CPC .......... *C08F 255/02* (2013.01); *A61L 29/049* (2013.01); *C08F 8/00* (2013.01);
(Continued)

(58) Field of Classification Search
None
See application file for complete search history.

(56) References Cited

U.S. PATENT DOCUMENTS 4,727,120 A * 2/1988 Nogues ................. C09J 151/06
525/168
5,214,091 A   5/1993 Tanaka
(Continued)

FOREIGN PATENT DOCUMENTS

| CN | 101055422 A | 10/2007 |
|----|-------------|---------|
| JP | 50-112494 A | 9/1975 |
| JP | 5232796 B2 | 7/2013 |

OTHER PUBLICATIONS

PCT International Search Report and Written Opinion in PCT/US2013/056176, dated Jun. 4, 2014, 12 pages.
(Continued)

*Primary Examiner* — Robert C Boyle
(74) *Attorney, Agent, or Firm* — Servilla Whitney LLC

(57) ABSTRACT

A novel amphiphilic graft copolymer is described. A process to make amphiphilic graft copolymers via grafting either poly(ethylene oxide) or polylactide side chains onto an EVA platform using oxo-anion ring-opening polymerization chemistry is also described. Polyethylene or polypropylene based graft copolymers are prepared starting from poly(ethylene-co-vinyl acetate) or maleic anhydride grafted isotactic polypropylene respectively. The amphiphilic character will result from the incorporation of hydrophilic poly(ethylene oxide) (PEO) side-chains. Various applications of the novel amphiphilic graft copolymer are also described including, but not limited to, thermoplastic elastomer, films, fibers, fabrics, gels, breathable packaging materials, additive for biodegradable system, surfactant, antistatic additives, polymer compatibilizers, phase transfer catalysts, solid
(Continued)

polymer electrolytes, biocompatible polymers, or incorporation into the materials listed above.

26 Claims, 23 Drawing Sheets

Related U.S. Application Data division of application No. 13/973,283, filed on Aug. 22, 2013, now Pat. No. 9,150,674.

(60) Provisional application No. 61/691,964, filed on Aug. 22, 2012.

(51) Int. Cl.
| | | |
|---|---|---|
| C08F 22/06 | (2006.01) | |
| C08F 22/10 | (2006.01) | |
| C08L 71/02 | (2006.01) | |
| C08J 5/18 | (2006.01) | |
| C08G 65/26 | (2006.01) | |
| C08F 8/04 | (2006.01) | |
| C08F 8/34 | (2006.01) | |
| C08F 8/44 | (2006.01) | |
| A61L 29/04 | (2006.01) | |
| C08L 23/06 | (2006.01) | |

(52) U.S. Cl.
CPC ............... *C08F 8/04* (2013.01); *C08F 8/34* (2013.01); *C08F 8/44* (2013.01); *C08F 22/06* (2013.01); *C08F 22/10* (2013.01); *C08G 65/2603* (2013.01); *C08G 65/2609* (2013.01); *C08G 65/2696* (2013.01); *C08J 5/18* (2013.01); *C08L 23/06* (2013.01); *C08L 71/02* (2013.01); *C08F 2800/20* (2013.01); *C08F 2810/50* (2013.01); *C08G 2650/24* (2013.01); *C08J 2323/08* (2013.01); *C08J 2351/06* (2013.01); *C08J 2451/06* (2013.01)

(56) References Cited

U.S. PATENT DOCUMENTS

| | | | |
|---|---|---|---|
| 5,292,803 A | | 3/1994 | Ohmae |
| 5,424,150 A | * | 6/1995 | Ohnishi ............. C08G 65/2609 252/182.1 |
| 6,433,080 B1 | | 8/2002 | Fujiki |
| 2008/0003493 A1 | * | 1/2008 | Bates .................. H01M 2/0207 429/66 |
| 2008/0273820 A1 | | 11/2008 | Wiker |
| 2010/0111167 A1 | | 5/2010 | Wu |

OTHER PUBLICATIONS

Gugliuzza, et al., "Role of additives in the water vapor transport through block co-poly(amide/ether) membranes: effects on surface and bulk polymer properties", European Polymer Journal 40, 2004, 2381-2389.

Jonquieres, et al., "Permeability of block copolymers to vapors and liquids", Prog. Polym. Sci. 27, 2002, 1803-1877.

Metz, et al., "Gas-Permeation Properties of Poly(ethylene oxide) Poly(butylene terephthalate) Block Copolymers", Macromolecules 37, 2004, 4590-4597.

Metz, et al., "Water vapor and gas transport through a poly(butylene terephthalate) poly(ethylene oxide) block copolymer", Desalination 148, 2002, 303-307.

Mueller, et al., "Breathable Polymer Films Produced by the Microlayer Coextrusion Process", Journal of Applied Polymer Science, vol. 78, 2000, 816-828.

Nandi, et al., "Open-pore morphology of i-PP copolymer crystallized from a gel state in supercritical propane", Polymer 45, 2004, 4819-4827.

Sirkar, "Membranes, Phase Interfaces, and Separations: Novel Techniques and Membranes—An Overview", Ind. Eng. Chem. Res. 47, 2008, 5250-5266.

Winter, et al., "Rigid Pore Structure from Highly Swollen Polymer Gels", Macromolecules 35, 2002, 3325-3327.

\* cited by examiner

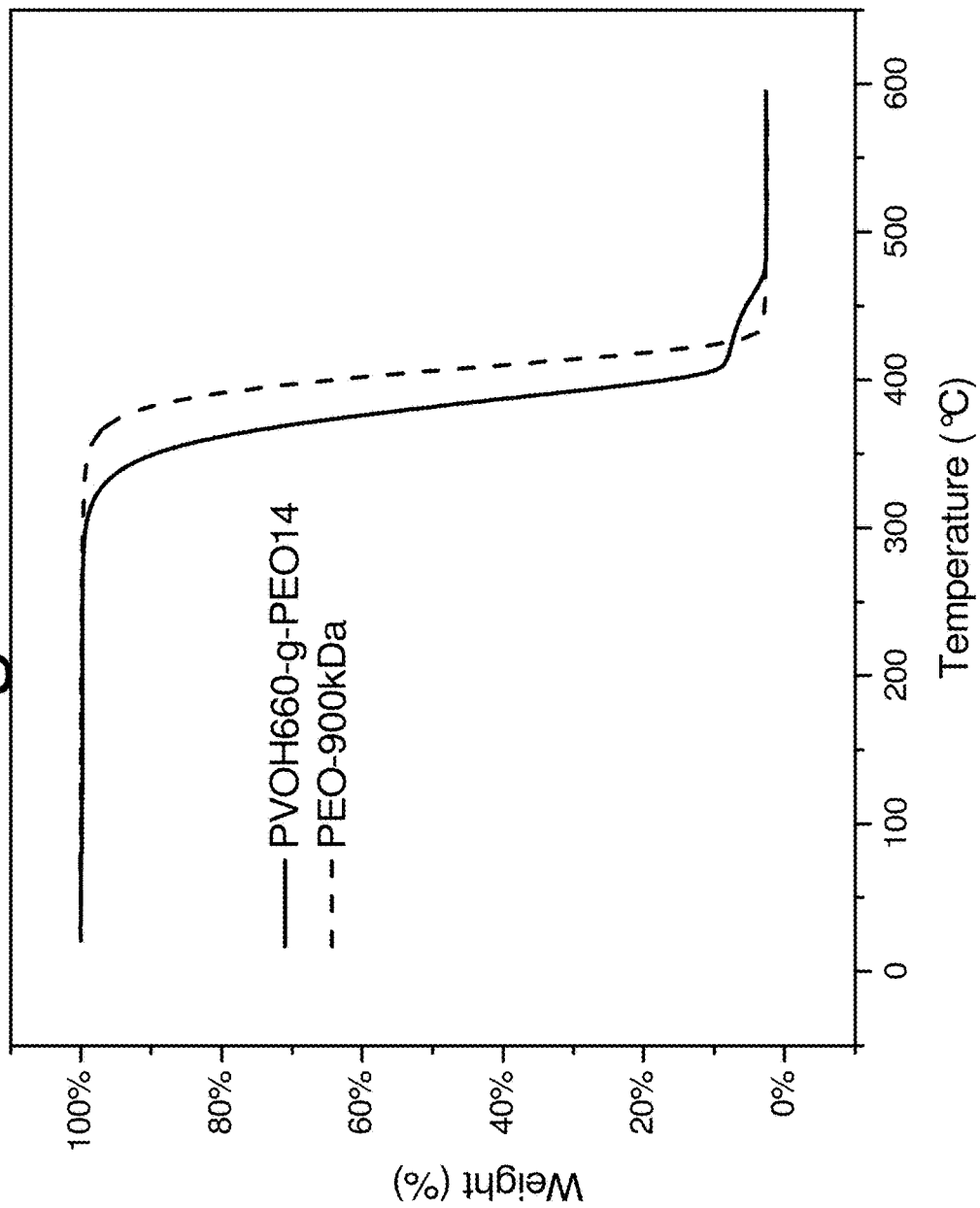

Figure 5

| 1mg/mL (in Water) | EO Units in Brush (n)[c] | Clear Point (°C) | Cloudy Point (°C) |
|---|---|---|---|
| PVOH360-g-PEO5 | 63 | 55 | 45 |
| PVOH460-g-PEO3.5 | 62 | 80 | 70 |
| PVOH460-g-PEO3 | 55 | 90 | 80 |
| PVOH460-g-PEO7 | 122 | 30 | Clear N.A. |

Figure 19

| IDENTIFICATION OF MATERIAL | PERMEABLE MATERIAL AEROSOL TEST | | | GURLEY DENSOMETER TEST (Seconds per 100cc) |
|---|---|---|---|---|
| | AIR FLOW RATE (LPM) | % PENETRATION | SAMPLES WITH >0.1% PENETRATION | BEFORE STERILIZATION |
| Film A | 0.00 | 0.011 | 0 | 10,160 |
| Film B | 0.00 | 0.080 | 0 | 49,504 |
| Film C | 4.31 | 3.789 | 1 | 0.7 |

Figure 21
Contact Angles

| Samples | Smooth surface | | | Porous surface | | |
|---|---|---|---|---|---|---|
| | Static Angles | Advancing Angles | Receding Angles | Static Angles | Advancing Angles | Receding Angles |
| Z-N LLDPE (100%) | 96 | 103 | 83 | n/a | n/a | n/a |
| Z-N LLDPE (90%), PEO 200kDa (10%) | 79 | 84 | 62 | n/a | n/a | n/a |
| Z-N LLDPE (55%), PEO 200kDa (45%) | 59 | 63 | 19 | 85 | 93 | 54 |
| Z-N LLDPE (90%), PVOH760-g-PEO7(10%) | 71 | 77 | 45 | n/a | n/a | n/a |
| Z-N LLDPE (84%), PVOH760-g-PEO7(6%), PEO (10%) | 50 | 65 | 10 | 64 | 76 | 35 |
| Z-N LLDPE (70%), PVOH760-g-PEO7(5%), PEO (25%) | 32 | 47 | 6 | 50 | 62 | 7 |
| Z-N LLDPE(51.33%), PVOH760-g-PEO7(3.67%), PEO (45%) | 14 | 31 | 9 | 69 | 75 | 32 |
| Z-N LLDPE (70%), PVOH660-g-PEO14(5%), PEO (25%) | 17 | 37 | 7 | 48 | 53 | 5 |

AMPHIPHILIC GRAFT COPOLYMERS

CROSS-REFERENCE TO RELATED APPLICATIONS

This application is a continuation of U.S. patent application Ser. No. 14/834,638, now allowed, filed Aug. 25, 2015, which is divisional of U.S. patent application Ser. No. 13/973,283, filed Aug. 22, 2013, now U.S. Pat. No. 9,150, 647, which claims priority under 35 U.S.C. § 119(e) to U.S. Provisional Appln. No. 61/691,964, filed Aug. 22, 2012, the disclosures of which are incorporated herein by reference in their entireties.

TECHNICAL FIELD

An aspect of the present invention relates generally to novel amphiphilic graft copolymers. Specifically, polyethylene or polypropylene based graft copolymers are disclosed as being prepared from poly(ethylene-co-vinyl acetate) or maleic anhydride grafted isotactic polypropylene, respectively. Also described is a process to make amphiphilic graft copolymers via grafting either poly(ethylene oxide) or polylactide side chains onto an ethylene vinyl acetate platform or maleic anhydride grafted polypropylene platform using oxoanion ring-opening polymerization chemistry. Various applications of the novel amphiphilic graft copolymers are also described including, but not limited to, thermoplastic elastomer, films, fibers, fabrics, gels, breathable packaging materials, additive for biodegradable systems, surfactant, antistatic additives, polymer compatibilizers, phase transfer catalysts, solid polymer electrolytes, biocompatible polymers, and incorporation into the materials listed above.

BACKGROUND

Ethylene vinyl acetate (EVA) copolymers are commodity materials with weight percentages of vinyl acetate that usually varies from 2 to 40%. EVA copolymers are comparable to elastomeric materials in softness and flexibility, yet EVA copolymers can be processed like other thermoplastics. EVA copolymers have good clarity and gloss, good barrier and water proof properties, low-temperature toughness, desirable sealant properties, and resistance to UV radiation. They are inherently tough, resilient and more flexible than low density polyethylene over a broad temperature range, and have excellent environmental stress crack resistance.

Polyethylene (PE), Ethylene vinyl acetate (EVA), and polypropylene (PP) are common resins in packaging film and medical device applications. EVA is a common sealant in film packaging and is currently used extensively in primary packaging applications, including both film-film and paper-film applications, as well as components of medical devices. Polypropylene can be used as the structural component of packaging films and as components of many medical devices.

Polymer films for medical device and packaging must meet a broad range of stringent criteria which include: a) functional requirements of the product post-sterilization; b) providing a sterile barrier and structural support for the product over its lifetime after sterilization when used in primary packaging applications; c) being capable of high fabrication rates with a broad fabrication window; d) being cost effective; and e) meeting increasing demands for environmental stewardship.

Beyond the United States and European countries, radiation based sterilization techniques are not readily available and ethylene oxide (EtO) sterilization is the primary mode of sterilization used. A breathable package is required for EtO sterilization. Additionally, non-breathable film-film packages are currently limited with respect to the geographical markets they can be used due to limitations of the altitude the package can experience without potentially incurring open seals. At high altitudes the air within the non-breathable package expands and can cause open seals, resulting in loss of sterility of the product. Paper top webs are common alternatives used in packaging; however, they usually require an adhesive coating which increases the cost. Moreover, paper is susceptible to tearing and punctures, which can result in the loss of sterility of the product, and possible product recalls. Direct seal paper packaging is paper packaging without an adhesive coating. Although direct seal paper packaging is a low cost alternative, it is difficult to process on current packaging machines and can have a narrow seal performance window between weak, open seal or strong seal which result in fiber tear or tearing of the paper. Both the weak seal and paper tears of direct seal paper packaging compromise the sterility of the product. Breathable non-paper films, such as Tyvek®, can be used but they are substantially more costly than conventional films. PEBAX® is a commercially available polyamide/polymer ether copolymer which offers breathability and steam sterilization capabilities while maintaining a sterile barrier. However, like Tyvek®, PEBAX® is a specialized and expensive material.

An approach to achieving breathability of a polymeric film is the concept of micro-perforated films, which is utilized in a wide variety of commercial applications, commonly in food packaging and medical & health applications. The food packaging applications primarily apply to fresh product wrapping to enhance shelf life, but are also used in wrapping things such as fresh breads and other baked goods. These micro-perforated films are tailored to have very selective permeation rates to oxygen, carbon dioxide, and moisture. The controlled moisture vapor transmission rate (MVTR) preserves the moisture of the produce and extends its sellable shelf life. Alternatively, perforated films are also used in medical and health applications. These films typically have larger perforations thus resulting in poor physical properties and very high MVTR. These films include applications like breathable sheets for diapers and feminine hygiene products, wound dressings, exam and surgery room paper, etc. These films would not have the proper breathability to maintain a microbial barrier or the required physical properties for primary packaging of medical devices.

Other approaches to achieving breathability in packaging film are the use of rigid fillers, such as talc, and application of a post-fabrication stretching to the film. However, the use of rigid fillers results in a film having poor structural integrity and pores which would not maintain a microbial barrier. Moreover, the residual rigid filler would contaminate the medical device within the package.

It is desirable to incorporate functional properties onto known polymers to provide desired traits, such as breathability. However, the incorporation of novel chemistries along the polymer chain backbone cannot readily be achieved using known addition polymerization processes of polyethylene or polypropylene without a complicated secondary reactive process or via a step-growth process. The secondary chemical modification processes are often not 100% effective or chemically pure, resulting in incomplete and undesirable secondary reactions which detrimentally alter the ultimate chemical, thermal, and physical properties of the final polymer. The chain-growth process, the process by which block copolymers are produced, is a multi-step process which is complex, time consuming, and costly. While high levels of molecular homogeneity, including a relatively narrow dispersity index, can be achieved on a laboratory scale, large scale commercial processes using known addition polymerization process of polyethylene produce a mix of mono- and various multi-block structures and a broad dispersity index.

Thus, there is a need for a process capable of modifying EVA and maleic anhydride grafted isotactic polypropylene copolymers by allowing the incorporation of amphiphilic side chains onto the polymer chain backbone at high levels of molecular homogeneity, including a relatively narrow dispersity index. There is also a need for an improved thermoplastic elastomer or commodity resin that would allow for ethylene oxide sterilization in practical packaging and medical device applications.

SUMMARY

One embodiment of the present invention pertains to an amphiphilic copolymer of the formula (I):

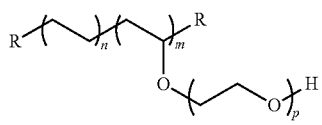
(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar values of n is in the range from 60 to 98 mole percent; and p is in the range of 5 to 500 ethylene oxide units.

Another embodiment of the present invention pertains to an amphiphilic copolymer of the formula (II):

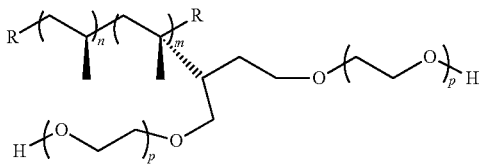
(II)

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units is in the range from 2 to 10 mole percent; the molar values of propylene units is in the range from 98 to 90 mole percent; and p is in the range of 5 to 500 ethylene oxide units.

Yet another embodiment of the present invention pertains to a process for preparing amphiphilic polyethylene-based copolymers comprising obtaining an ethylene vinyl acetate copolymer having between 2-40 weight percent of vinyl acetate; reacting the ethylene vinyl acetate copolymer with potassium methoxide to prepare a mixture of polymeric potassium alkoxide and methyl acetate co-product; performing distillation on the a mixture of polymeric potassium alkoxide and methyl acetate co-product to remove the methyl acetate co-product; performing ethylene oxide ring-opening polymerization on the polymeric potassium alkoxide; removing aliquots during the ethylene oxide ring-opening polymerization to allow for systemic variation in degree of polymerization of ethylene oxide side chains; and collecting an amphiphilic polyethylene based graft co-polymer having the structure of formula (I):

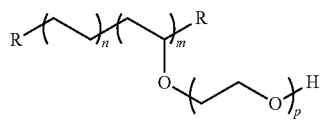

wherein the molar value of m is in the range from 2 to 40 mole percent; the molar values of n is in the range from 60 to 98 mole percent; and p is in the range of 5 to 500 ethylene oxide units.

According to one embodiment of the process of the present invention, the molar values of m is in the range from 10 to 40 mole percent. According to another embodiment, the molar values of n is in the range from 60 to 90 mole percent for n. According to one embodiment, the molar values of p is in the range from 5 to 400.

In one or more embodiments, the ethylene vinyl acetate copolymer has a melt index from 0.3 to 500 dg/min.

In one or more embodiments, the ethylene oxide ring-opening polymerization is performed at a reaction temperature in the range of –20 to 100° C. In a specific embodiment, the ethylene oxide ring-opening polymerization is performed at a reaction temperature greater than 30° C. In yet another specific embodiment, the ethylene oxide ring-opening polymerization is performed at a reaction temperature of 60° C.

In one or more embodiments, the ethylene oxide ring-opening polymerization is performed under alkaline conditions.

In one or more embodiments, the ethylene oxide ring-opening polymerization is performed using 1,3 propane sultone.

In one or more embodiment, the amphiphilic polyethylene based graft co-polymer has a dispersity index in the range of 2 to 10.

Yet another embodiment of the present invention pertains to a process for preparing amphiphilic polypropylene-based copolymers comprising obtaining an maleic anhydride grafted polypropylene wherein the molar percentages of grafted maleic anhydride units is in the range from 2 and 10 mole percent; the molar values of propylene units is in the range from 98 to 90 mole percent; reacting the maleic anhydride grafted polypropylene with a reducing agent to prepare a iPP-diol copolymer, wherein the diol content is equal to the molar percentage of the originally grafted maleic anhydride units:

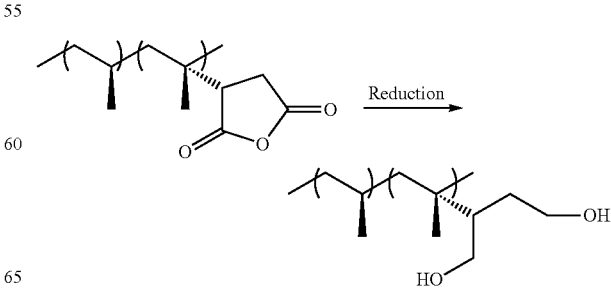

and subsequently performing ethylene oxide ring-opening polymerization on the iPP-diol copolymer; and isolating an amphiphilic iPP-g-PEO copolymer having the structure

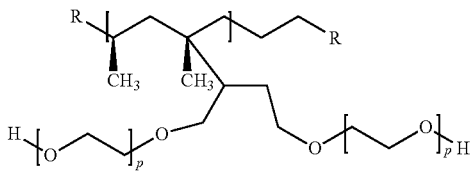

wherein R represents the end-groups present in either Ziegler-Natta or metallocene catalyzed polypropylene including, but not limited to, hydrogen, alkyl, substituted alkyl, vinylic substituted alkyl, hydrocarbyl, substituted hydrocarbyl, or vinylic substituted hydrocarbyl group; the molar percentages of grafted maleic anhydride units is in the range from 2 to 10 mole percent, the amount of diol after reduction of the maleic anhydride is in the range from 2 to 10 mole percent; the molar values of propylene units is in the range from 98 to 90 mole percent; and p is in the range of 5 to 500.

According to one or more embodiment of the process of the present invention, the molar percentage values of propylene is in the range from 90 to 98 mole percent, the molar values of diol derived from reduction of maleic anhydride is in the range from 10 to 2 mole percent, and the molar values of p is in the range from 5 to 400 mole percent.

According to one or more embodiment of the process of the present invention, the ethylene oxide ring-opening polymerization is performed at a reaction temperature in the range of −20 to 100° C. In one embodiment, the ethylene oxide ring-opening polymerization is performed at a reaction temperature greater than 30° C. In another embodiment, the ethylene oxide ring-opening polymerization is performed at a reaction temperature of 90° C.

According to one or more embodiment of the process of the present invention, the ethylene oxide ring-opening polymerization is performed under alkaline conditions.

According to one embodiment of the process of the present invention, the ethylene oxide ring-opening polymerization is performed using 1,3 propane sultone.

According to one embodiment of the present invention, the amphiphilic iPP-g-PEO copolymer has a dispersity index in the range of 2 to 8.

Another aspect of the present invention pertains to an additive, compatibilizer, thermoplastic elastomer or breathable top web film comprising the amphiphilic copolymer of the present invention.

BRIEF DESCRIPTION OF THE DRAWINGS

FIG. 4 shows a graphical representation of Thermo Gravimetric Analysis of a graft copolymer.

FIG. 5 shows test results correlating side chain length and clarity upon dissolution of grafted polymers in water as a function of temperature.

FIG. 19 shows permeability results of two sample grafted polymer films and a non-grafted film blends.

FIG. 21 shows the contact angles of various samples of grafted and non-grafted films.

DETAILED DESCRIPTION

Figure 1:
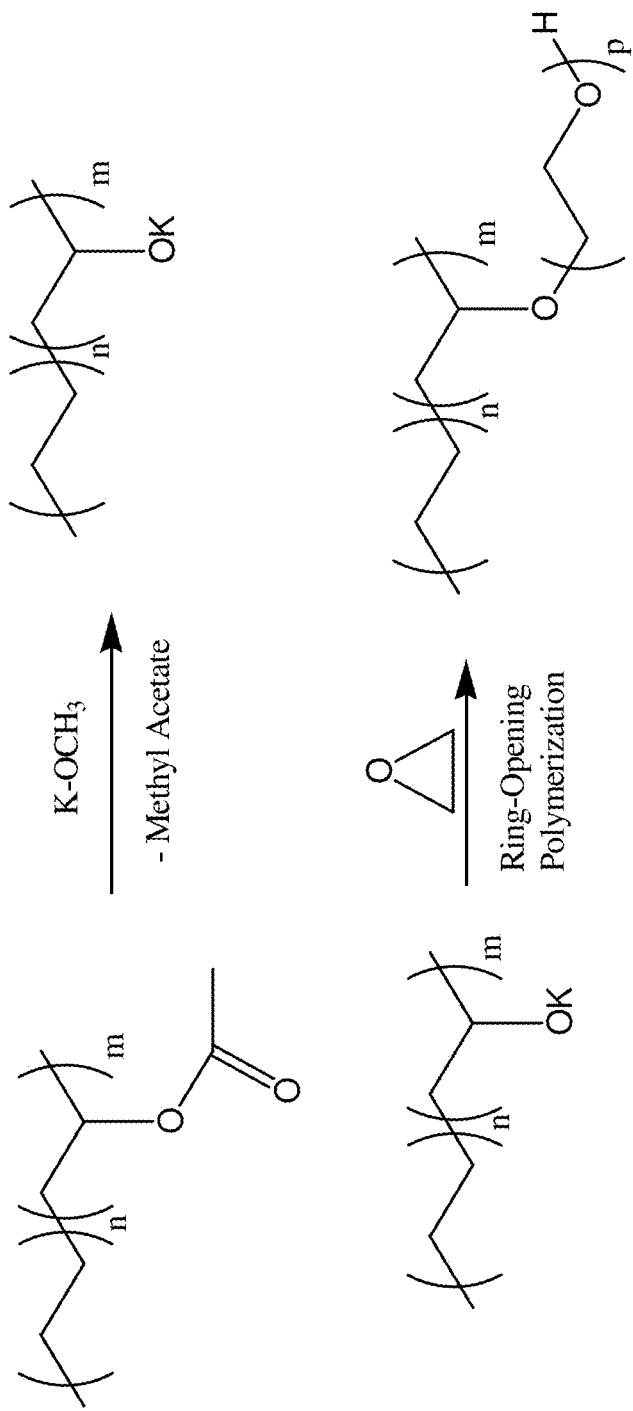
FIG. 1 shows a synthetic scheme for the preparation of polyethylene based graft copolymers using a poly(ethylene-co-vinyl acetate) starting material.

Before describing several exemplary embodiments of the invention, it is to be understood that the invention is not limited to the details of construction or process steps set forth in the following description. The invention is capable of other embodiments and of being practiced or being carried out in various ways.

In general, the present invention describes a process for the chemical modification of commodity polyolefins via a chemical grafting-approach to develop novel amphiphilic copolymers having general structures (I) and (II):

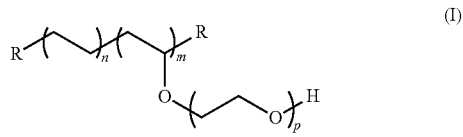

(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent and p is in the range of 5 to 500 ethylene oxide units;

and

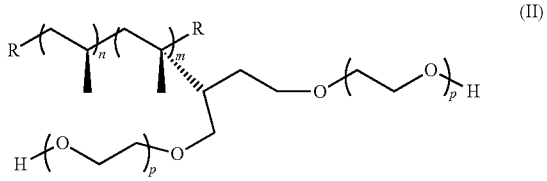

(II)

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units is in the range from 2 to 10 mole percent, the amount of diol after reduction of the maleic anhydride, is in the range from 2 and 10 mole percent; the molar values of propylene units is in the range from 98 to 90 mole percent and p is in the range of 5 to 500 ethylene oxide units.

By utilizing the vinyl acetate functionality along the polyethylene (PE) backbone or maleic anhydride functionality along the polypropylene backbone of a commodity resin to create a grafting side group, a very broad range of functional chemistries could be ultimately incorporated. The potential applications of these functionalized polymeric systems are equally as broad as discussed in detail below.

One or more embodiments of the present invention describe a process to make amphiphilic graft copolymers via grafting either poly(ethylene oxide) or polylactide side chains onto an ethylene vinyl acetate (EVA) platform or maleic anhydride grafted isotactic polypropylene platform using oxo-anion ring-opening polymerization chemistry. Table 1 shows an exemplary sample of ethylene vinyl acetate (EVA) platforms that may be used in the present invention and the Ziegler-Natta linear low density polyethylene used as a comparative and used as a blend component for samples in this patent. Table 2 shows an exemplary sample of polyvinyl alcohol-graft-poly(ethylene oxide) (PVOH-g-PEO) copolymers. Tables 1 and 2 is not an exhaustive list of EVA platforms and PVOH-g-PEO) copolymers that may be used in the present invention, but rather an exemplary list of EVA platforms and PVOH-g-PEO) copolymers that may be used in the present invention. Commercially available samples of poly(ethylene oxide) (PEO) of 5,000 and 200,000 g/mol were used, described herein as PEO 5 kDa and PEO 200 kDA, respectively were also used as blend components for samples in this patent.

TABLE 1

| Sample | Density (g/cc) ASTM D792 | MI (g/10 min) ASTM D1238 | By Weight Vinyl Acetate Comonomer content |
|---|---|---|---|
| Z. N. LLDPE | 0.92 | 1 | |
| EVA 360 | 0.948 | 2 | 25% |
| EVA 460 | 0.941 | 2.5 | 18% |
| EVA 660 | 0.933 | 2.5 | 12% |
| EVA 760 | 0.93 | 2 | 9.30% |

TABLE 2

| Nomenclature | Molecular Weight (kDa)[a] | Average —$CH_2$—$CH_2$— Intervals Number (Brush Density)[b] | Average EO Units in Brush (n)[c] | Mass Gain (%) |
|---|---|---|---|---|
| PVOH360-g-PEO1 | 112.1 | 14.0 | 16 | 182 |
| PVOH360-g-PEO2 | 176.9 | 14.0 | 31 | 346 |
| PVOH360-g-PEO5 | 320.4 | 14.0 | 63 | 707 |
| PVOH360-g-PEO6 | 414.0 | 14.0 | 84 | 943 |
| PVOH360-g-PEO7 | 476.4 | 14.0 | 98 | 1095 |
| PVOH460-g-PEO2 | 148.7 | 17.4 | 33 | 299 |
| PVOH460-g-PEO3 | 221.9 | 17.4 | 55 | 495 |
| PVOH460-g-PEO3.5 | 245.4 | 17.4 | 62 | 558 |
| PVOH460-g-PEO4 | 281.1 | 17.4 | 72 | 654 |
| PVOH460-g-PEO7 | 447.6 | 17.4 | 122 | 1100 |
| PVOH660-g-PEO2 | 180.6 | 25.3 | 51 | 314 |
| PVOH660-g-PEO3.5 | 283.4 | 25.3 | 89 | 550 |
| PVOH660-g-PEO14 | 994.6 | 25.3 | 352 | 2181 |
| PVOH760-g-PEO0.25 | 82.0 | 35.7 | 9 | 39 |
| PVOH760-g-PEO1.02 | 153.3 | 35.7 | 36 | 160 |
| PVOH760-g-PEO1.07 | 157.9 | 35.7 | 38 | 168 |
| PVOH760-g-PEO3.64 | 395.8 | 35.7 | 130 | 572 |
| PVOH760-g-PEO4.05 | 433.8 | 35.7 | 145 | 636 |
| PVOH760-g-PEO6.98 | 704.9 | 35.7 | 249 | 1097 |

[a]$M_n = M_{nPVOH}*(1 + n*44/28)$
[b]$D = (M_{nPVOH}/[OH])/28$
[c]$n = ([EO]/[E])/(28*[OH])$

As with regards to the nomenclature of the grafted copolymers described herein, eg. PVOH360-g-PEO7, the nomenclature to describe the graft copolymers prepared is PV OH-###-PEO*, where ### is in reference to the starting ethylene vinyl alcohol polymer, i.e. 360 refers to EVA 360. The integer number * is the ratio of ethylene oxide graft units, value p from FIG. 1, divided by the average number of ethylene units in the polymer backbone, value n from FIG. 1.

Polyethylene Based Materials

EVA's are commodity olefin-based polymers widely used in medical devices and readily commercially available in a broad range of percentage of vinyl acetate and molecular weights. Ethylene vinyl acetate (EVA) copolymers have weight percentages of vinyl acetate that usually varies from 2 to 40%. EVA copolymers approach elastomeric materials in softness and flexibility, yet can be processed like other thermoplastics. Ethylene vinyl acetate (EVA) copolymers have good clarity and gloss, barrier properties, low-temperature toughness, stress-crack resistance, hot-melt adhesive, water proof properties, and resistance to UV radiation.

In one or more embodiments, the process of the present invention utilizes commercially produced ethylene vinyl acetate (EVA) as a starting material. These are olefinic polymers comprised of a polyethylene backbone with vinyl acetate groups along the backbone. Through modification of the vinyl acetate (VA) group, a polyethylene-based system is produced with side groups along the backbone of tailored chemical functionality. By utilizing the existing vinyl acetate side chain of a commercially produced ethylene vinyl acetate copolymer, the modification points are fixed during the EVA synthesis process and the polyethylene backbone is not altered during the chemical modification process. The starting EVA for the present invention is preferably prepared by a high pressure free radical copolymerization of ethylene and vinyl acetate, with the end-groups of the starting material and resultant grafted copolymer being dictated by the radical initiator employed and the reactions conditions under which the copolymerization was performed. A suitable commercially available polymer may be chosen as the starting point since the necessary functional group, a hydroxyl group, has already been incorporated onto the polylolefin backbone as a consequence of the polymerization chemistry. Various commercially available hydrolyzed EVAc polymer, ethylene vinyl alcohols, and EVAc sources may be used as a suitable starting material/substrate to prepare the graft copolymers of the present invention, including but not limited to, i.e. Elvax® resins (DuPont™), Elevate® (Westlake Chemical™), and Ultrathene® (Lyondell Basell™). Because the process of the present invention maintains the PE backbone of the starting material, the end-groups of the resultant graft copolymer will governed by the starting EVA starting material. As will other basic materials properties, for example, the length of ethylene units present in the EVA copolymer are not changed during grafting from polymerization and therefore the backbone melting point will only be slightly altered. The number of modification sites would be dependent on the percentage of vinyl acetate incorporated along the polyethylene backbone of the starting material. Through the modification of the VA side chains, the process of the present invention can be used to produce a polyethylene (PE) copolymer with highly tailorable functionality. Unlike other modification processes known in the art, the process of the present invention maintains the PE backbone and does not detrimentally impact the dispersity of the PE, or result in undesirable side or secondary reactions. Maintenance of a narrow dispersity index (PDI) is an indication that cross-linking and/or chain scission did not occur. The present invention maintains a narrow molecular weight distribution for the grafted side arm. The desired dispersity index of resultant grafted copolymers of the present invention is preferably in the range of 1.05 to 1.25.

In one embodiment of the present invention, polyethylene based graft copolymers will be prepared from a poly(ethylene-co-vinyl acetate) starting material as shown in FIG. 1. Controlled ring-opening polymerization is used to graft polymer side chains of ethylene oxide onto the polyethylene backbone to prepare polyethylene-graft-poly(ethylene oxide) (PE-g-PEO) copolymers having functionalized side groups. Incorporation of hydrophilic poly(ethylene oxide) (PEO) side-chains onto the polyethylene backbone will result in a copolymer with desired amphiphilic characteristics. The grafting density of the PEO side chains can be varied by the choice of the composition of the starting EVA copolymer. EVA compositions with higher vinyl acetate content will give higher grafting frequency along the backbone, with the consequence being fewer ethylene units between branches and thus afford a means of controlling back bone melting characteristics. The ratio of hydrophobic to hydrophilic content in the graft copolymers can be independently adjusted by the extent of ethylene oxide polymerization. In one or more embodiments, copolymers of ethylene and vinyl acetate ranging in vinyl acetate content from 9 to 40% and melt indexes from 0.3 to 500 dg/min may be used as platform materials. A exemplary starting material may have the following structure:

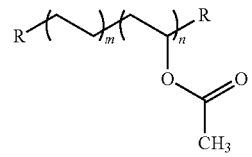

As shown in FIG. 1, the amphiphilic graft copolymers of the present invention are prepared in a two-step synthetic sequence. First, a hydrolysis reaction is performed on the EVA platform whereby the acetate units are removed to produce ethylene vinyl alcohol copolymers (EVOH) and a methyl acetate co-product. In one embodiment of the present invention, the acetate units will be removed by reaction with potassium methoxide and the co-product methyl acetate will be removed by distillation. The resultant polymeric potassium alkoxide is then used to initiate ethylene oxide ring-opening polymerization (ROP). In the second step of the process, oxo-anion polymerization is performed on the copolymers of ethylene and vinyl acetate to produce a broad range of novel polyethylene based graft-copolymers.

The content of hydroxyl units and sequence length of the ethylene units along the backbone of the starting material is variable. This sequence length of the ethylene units along the backbone dictates the corresponding melting point of the copolymer, as well as, the eventual strength of the final product. The oxo-anion polymerization step of the present invention allows for a well-controlled grafting from approach for the generation of graft copolymers. The chemical nature of the grafts can be varied to include side groups including, but not limited to, poly(ethylene oxide), polylactide, polyglycolide, polycaprolactone or polyester copolymers. The grafted side-arms can be either crystalline or amorphous, hydrophilic or hydrophobic, and either robust or susceptible to hydrolysis.

The reaction conditions will be such that the ROP will proceed in a living manner. The resulting graft copolymers will have a narrow dispersity of side-chain graft lengths and a ratio of weight average molecular weight to number average molecular weight from 1.05 to 1.25. Two general reaction schemes can be considered for promoting the oxo-anionic ring-opening polymerization. One general reaction scheme for promoting the oxo-anionic ring-opening polymerization is the use of alkoxide salts derived from deprotonation of EVOH copolymers with potassium, rubidium or cesium as counter ions. A second general reaction scheme for promoting the oxo-anionic ring-opening polymerization is the use of organo-catalysis directly from the EVOH copolymers. Monomers for the grafting polymerization can be selected from the range of cyclic monomer that are known to undergo oxo-anion ring-opening polymerization including, but not limited to, ethylene oxide, oxetane, and cyclic esters including lactides and lactones.

The selection of reaction conditions to perform controlled oxo-anionic ring-opening polymerization includes the use of anhydrous solvents and reaction temperature in the range of −20 to 100° C. A reaction temperature greater than 30° C. is preferred to produce higher reaction rates. Reaction pressures will vary according to reaction compositions. A reaction pressure equal to, or slightly greater than, atmospheric pressure is preferred. A narrow dispersity of side-chain graft lengths is preferred. Removal of aliquots during ROP will allow for systematic variation in the degree of polymerization of the ethylene oxide side chains. Molecular weight and side chain graft density of the resultant polyethylene-graft-poly(ethylene oxide) (PE-g-PEO) copolymers will be a function of the starting EVA copolymer, and the degree of polymerization will be a direct function of the length of time the ROP is performed. Therefore, the process of the present invention allows for an excellent level of control over the values of n, m and p. The selection of the range of molar values of n, m and p can span the range from 2 to 40 mole percent for the m, 60 to 98 mole percent for n, and 5 to 500 ethylene oxide units for p. The preferred ranges will encompass those values of n, m and p that are present in readily available EVAc copolymers. Thus, the process of the present invention allows for a broad range of control over resultant compositions of copolymer.

Solvents to perform controlled oxo-anionic ring-opening polymerization of the present invention can be selected from a range of polar aprotic solvents or a mixture of such solvents including, but not limited to, tetrahydrofuran, diglyme, toluene, or mixtures thereof.

Compositional analysis of the resultant graft copolymers of the present invention may be determined using $^1$H and $^{13}$C NMR spectroscopy, as well as, molecular weight analysis using gel-permeation chromatography.

Figure 2:
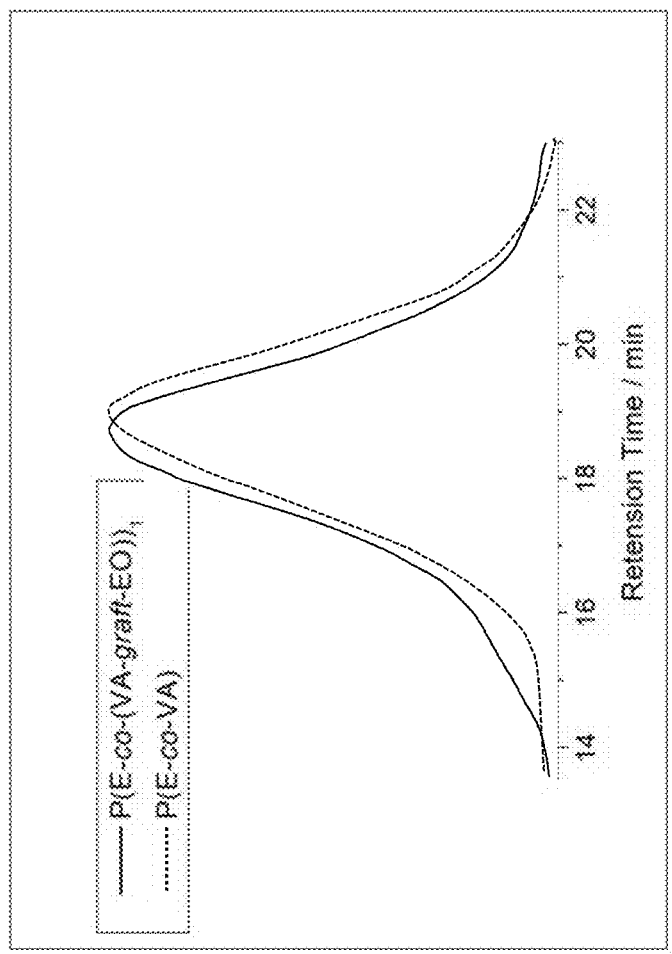
FIG. 2 shows the increase in molecular weight as observed by GPC for the grafting of ethylene oxide from an ethylene-co-vinyl acetate copolymer.

As shown in FIG. 2 and Table 3, the increase in molecular weight is observed by GPC for the grafting of ethylene oxide from an ethylene-co-vinyl acetate copolymer. The increase in molecular weight of the grafted copolymers is evident from the earlier elution times observed by gel permeation chromatography (GPC). Representative data is shown in FIG. 2 and Table 3 for the grafting of ethylene oxide from the random copolymer of ethylene and vinyl alcohol, that was derived by hydrolysis of the corresponding ethylene (vinyl acetate) random copolymers. The molecular weight data presented in Table 3 shows the PDI (polydispersity index or dispersity index) is maintained for the grafting of ethylene oxide from an ethylene-co-vinyl acetate copolymer, indicating a degradation of the polymer backbone or crosslinking does not occur during the grafting reaction process.

Tabulated molecular weight data is provided below in Table 3.

TABLE 3

| Polymer | $M_n$ [kDa] | $M_w$ [kDa] | PDI |
|---|---|---|---|
| P(E-co-(VA-graft-EO))$_1$ | 78.2 | 226.2 | 2.90 |
| P(E-co-VA) | 52.0 | 148.6 | 2.85 |

As the degree of polymerization of the ethylene oxide side chains increases, the poly(ethylene oxide) (PEO) side chains exceed the critical molecular weight needed to become semi-crystalline and thus the side-chains will crystallize. By utilizing the VA functionality along the PE backbone to create a grafting side group, a very broad range of functional chemistries could be ultimately incorporated by the process of the present invention. The potential application of these functionalized polymeric systems would be equally as broad.

Thermal analysis by differential scanning calorimetry (DSC) can be used to determine glass transitions temperature and melting points of the resultant semi-crystalline graft copolymers. Thermal analysis by DSC may be used to establish the expected dual semi-crystalline character of the resultant copolymers, and thermogravimetric analysis (TGA) may be performed to provide an indication of the upper limit of temperature stability of the resultant copolymers.

Figure 3A:
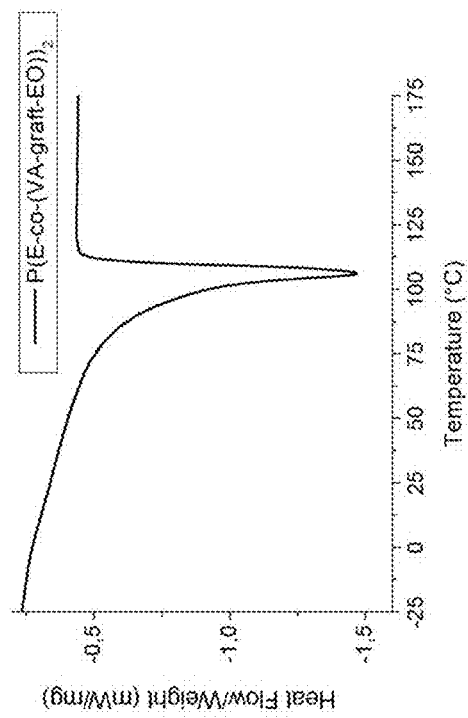
FIG. 3a shows differential scanning calorimetry scans of EVA grafted with short ethylene oxide side chains.
Figure 3B:
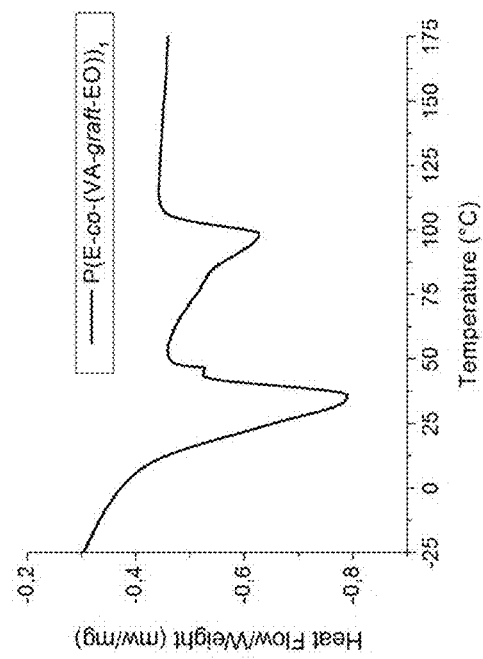
FIG. 3b shows differential scanning calorimetry scans of EVA grafted with long ethylene oxide side chains.

As shown in FIGS. 3a and 3b, DSC scans highlight the ability of the grafting process of the present invention to create an amorphous or semi-crystalline side chain by modification of the molecular weight of the side chain. FIG. 3a shows EVA grafted with short ethylene oxide side chains. FIG. 3b shows EVA grafted with long ethylene oxide side chains.

As shown in FIG. 4 and Table 4, the Thermo Gravimetric Analysis of a graft copolymer (PVOH 660-g-PEO14) to a PEO-900 kDa sample shows that stability of the graft copolymer is comparable with super high molecular weight commercial homopolymer PEO.

TABLE 4

| Graft polymers | PVOH660-g-PEO14 | PEO-900 kDa |
|---|---|---|
| Temperature @ 2% Weight loss | 320° C. | 360° C. |
| Char Residual | 2.6% | 2.5% |

To show controlled adhesion of the grafted films with PE, a sample of PE-g-PEO, pure PEO and HDPE were melt-pressed to thin films. PE-g-PEO and pure PEO thin films were melt-pressed onto HDPE film at 150° C. It was shown that PE-g-PEO can be well adhesive to the HDPE, but pure PEO has no adhesion to the HDPE at all.

As shown in FIG. 5, the frequency of the PEO along the PVOH backbone and the side chain length can govern when the polymer dissolves. FIG. 5 shows test results correlating side chain length and clarity upon dissolution of grafted polymers. As shown in FIG. 5, in instances whereby copolymers have the same PVOH backbone, the polymers with a longer brush have a lower clear and cloudy point. As shown in FIG. 5, in instances whereby copolymers have a similar brush length, the copolymers with higher brush density have a lower clear and cloudy point. Thus, as shown in FIG. 5, the miscibility point in water can be controlled through tailoring the side chain lengths and selection of the base resins in regards to the frequency of the side chains.

Table 5 shows a summary of the differential scanning calorimetry of various grafted copolymers.

TABLE 5

| Sample | PEO Tm (° C.) | Tc (° C.) | Heat Flow (J/g) | Crystallinity [a] |
|---|---|---|---|---|
| PVOH360-g-PEO1 | 18 | 57 | 34 | 17 |
| PVOH360-g-PEO2 | 40 | 54 | 82 | 40 |
| PVOH360-g-PEO5 | 52 | 28 | 119 | 58 |
| PVOH360-g-PEO6 | 54 | 30 | 126 | 61 |
| PVOH360-g-PEO7 | 62 | 39 | 126 | 62 |
| PVOH460-g-PEO3 | 51 | 25 | 89 | 43 |
| PVOH460-g-PEO3.5 | 53 | 29 | 97 | 47 |
| PVOH460-g-PEO7 | 55 | 32 | 135 | 66 |
| PVOH660-g-PEO2 | 51 | 24 | 94 | 46 |
| PVOH660-g-PEO3.5 | 54 | 32 | 113 | 55 |
| PVOH660-g-PEO14 | 61 | 39 | 157 | 77 |
| PVOH760-g-PEO0.25 | 20 | −39 | ~0 | ~0 |
| PVOH760-g-PEO1 | 44 | 12 | 42 | 21 |
| PVOH760-g-PEO4 | 64 | 31 | 125 | 61 |
| PVOH760-g-PEO7 | 66 | 31 | 131 | 64 |

[a] $\Delta H_{100\% \ crystallinity}$ = 205 J/g
J. Polym. Sci., Part B: Polym. Phys., 2006, 44, 3042-3052.

As shown in Table 5, the values of Tm, Tc and Crystallinity increase as the number of repeating unit increase on the brush. The polymerization degree of PEO can be established by the Tm of PEO.

Poly(Lactic Acid) (PLA)

In another embodiment of the present invention, the grafted side chains can comprise poly(lactic acid) (PLA) which produce a resultant copolymer having a dual semi-crystalline character. Poly(lactic acid) is a bio-compatible polymer that is derived from a renewable resource. Breathability would be achieved by selective hydrolysis of the polylactide side chains to generate porous membranes.

In one embodiment of the present invention, EVOH is used as a starting platform for the preparation of novel polyethylene-graft-polylactide copolymers (PE-g-PLA). The grafting density of the PLA side chains can be varied by the choice of the composition of the starting EVOH copolymer, and the ratio of hydrophobic to hydrolysable content can be independently adjusted by the extent of lactide polymerization. Lactide is derived from renewable resources and PLA is a bio-compatible polymer, thus conferring environmental benefits over conventional petroleum derived polyethylenes. Partial, or complete, hydrolysis of the grafted PLA side chains generates porosity in PE-g-PLA copolymers leading to breathability of membranes from these compositions with the added advantage that the extracted porogen is simply lactic acid.

Polypropylene Based Materials

Figure 6:
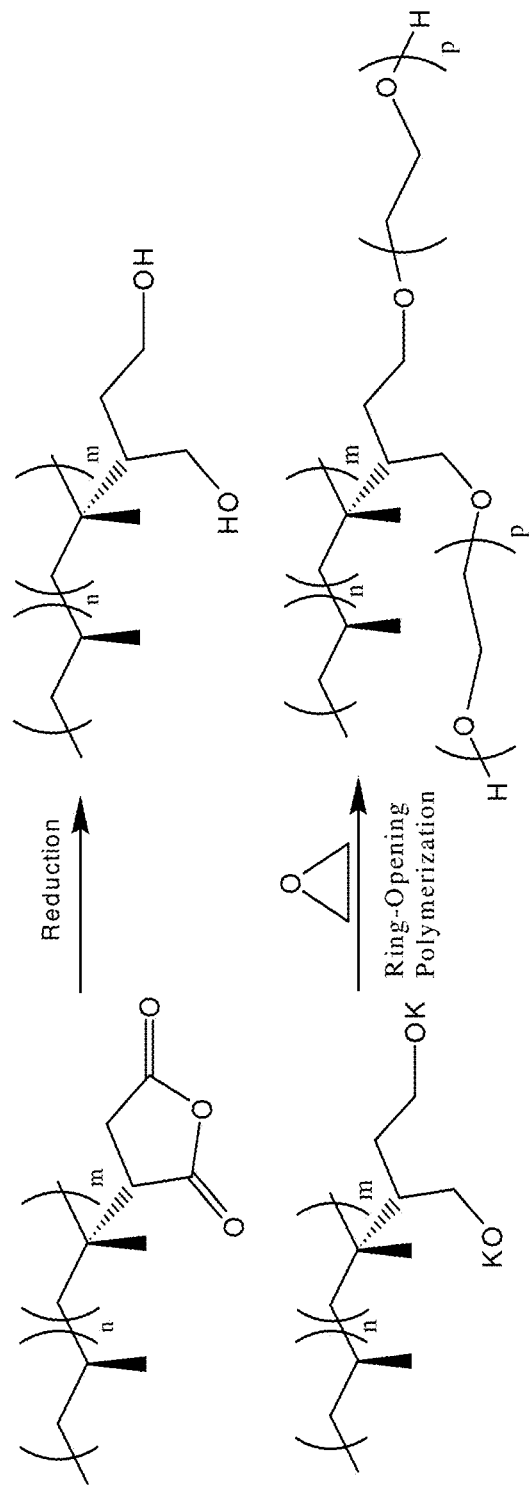
FIG. 6 shows a synthetic scheme for the preparation of polypropylene-graft-poly(ethylene oxide) using a maleic anhydride grafted polypropylene starting material.

In another embodiment of the present invention, polypropylene may be used as the polyolefin platform substrate. As shown in FIG. 6, the basic substrate will be maleic anhydride grafted polypropylene. Maleic anhydride grafted polypropylene is a commodity material available in a range of compositions.

The selection of preferred maleic anhydride grafted polypropylene will have molar percentages of grafted maleic anhydride units, and consequently the amount of diol after reduction of the maleic anhydride, in the range from 2 and 10 mole percent; and molar values of propylene units in the range from 98 to and 90 mole percent. The preferred ranges will encompass those values of grafted maleic anhydride that are present in readily available commercial maleic anhydride grafted polypropylene.

Yet another embodiment of the present invention pertains to a process for preparing amphiphilic polypropylene-based copolymers comprising obtaining an maleic anhydride grafted polypropylene wherein the molar percentages of grafted maleic anhydride units is in the range from 2 to 10 mole percent; the molar values of propylene units is in the range from 98 to 90 mole percent; reacting the maleic anhydride grafted polypropylene with a reducing agent to prepare a iPP-diol copolymer, wherein the diol content is equal to the molar percentage of the originally grafted maleic anhydride units;

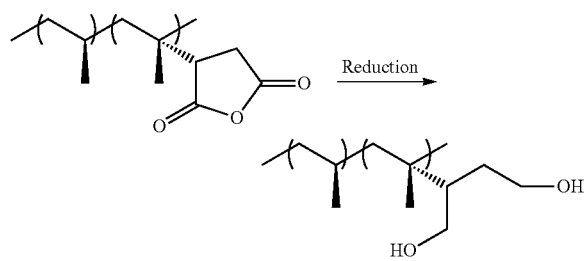

performing ethylene oxide ring-opening polymerization on the iPP-diol copolymer; and isolating an amphiphilic iPP-g-PEO copolymer having the structure

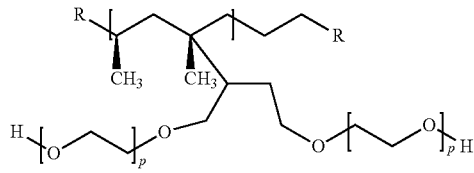

wherein R represents the end-groups present in either Ziegler-Natta or metallocene catalysized polypropylene including, but not limited to, hydrogen, alkyl, substituted alkyl, vinylic substituted alkyl, hydrocarbyl, substituted hydrocarbyl, or vinylic substituted hydrocarbyl group; the molar percentages of grafted maleic anhydride units is in the range from 2 to 10 mole percent, and consequently the amount of diol after reduction of the maleic anhydride is in the range from 2 to 10 mole percent; the molar values of propylene units is in the range from 98 to 90 mole percent, and p is in the range from 5 to 500.

According to one or more embodiments of the process of the present invention, the molar percentage values of propylene is in the range from 90 to 98 mole percent, the molar values of diol derived from reduction of maleic anhydride is in the range from 10 to 2 mole percent, and the molar values of p is in the range from 5 to 400 mole percent.

According to one or more embodiment of the process of the present invention, the ethylene oxide ring-opening polymerization is performed at a reaction temperature in the range of −20 to 100° C. In one embodiment, the ethylene oxide ring-opening polymerization is performed at a reaction temperature greater than 30° C. In another embodiment, the ethylene oxide ring-opening polymerization is performed at a reaction temperature of 90° C.

According to one or more embodiment of the process of the present invention, the ethylene oxide ring-opening polymerization is performed under alkaline conditions.

According to one embodiment of the process of the present invention, the ethylene oxide ring-opening polymerization is performed using 1,3 propane sultone.

According to one embodiment of the present invention, the amphiphilic iPP-g-PEO copolymer has a dispersity index in the range of 2 to 8.

Controlled oxo-anion ring-opening polymerization of ethylene oxide will yield novel compositions of iPP-g-PEO. The grafting density of the PEO side chains can be varied by the choice of the composition of the starting iPP-diol copolymer. The ratio of hydrophobic to hydrophilic content can be independently adjusted by the extent of ethylene oxide polymerization. The process of the present invention provides a broad range of control over sample compositions. Molecular weight and side chain graft density will be a function of the starting maleic anhydride grafted polypropylene, and the control over the side-chain length will be a direct function of the length of time the ROP of ethylene oxide is performed. Breathable films and membranes can be prepared from the PP-g-PEO copolymers, and blends thereof, by compression molding or film casting. Breathable membranes can be prepared from the PP-g-PEO copolymers.

The PP-g-PEO copolymers could also be used as compatibilizers between two incompatible polymeric systems with one component being PP-based, or having an affinity for PP, and the other having an affinity for PEO, enhancing the dispersion of the secondary phase and interaction between the two phases resulting in enhanced physical performance, as well as providing improved product consistency. The PP-g-PEO copolymers of the present invention may also be used as a toughening agent to increase the physical performance attributes of polypropylene, including impact, tear, or puncture resistance.

Other additives could be likewise be driven to the interface between the propylene and the secondary phase, such as exfoliated graphene or clay platelets for enhanced oxygen barrier properties. Oxygen scavengers could likewise be incorporated. Due to high level of dispersion and propensity for the additive to move to the blend interface, lower levels of additives would need to be incorporated for a higher level of performance and enhanced efficiency.

Fabrication methods for producing articles from the graft modified EVA-based copolymers, PE-g-PLA copolymers, or PP-g-PEO copolymers include, but are not limited to, monolayer or multi-layer films which are blown, cast, extruded, or extrusion coated. Final products may be made through injection molding, extrusion, blow molding, including the fabrication of fibers.

Additives that may be added to the graft modified EVA-based copolymers PE-g-PLA copolymers, or PP-g-PEO copolymers, blend or multilayer film comprising of the graft modified EVA-based copolymers, include but are not limited to, organic or inorganic particles such as talc, clay, wood or carbon fibers, oils, and other fillers including other polymeric materials, reinforcing agents, stabilizers, colorants, and processing aids.

Example 1: EVA Platform

In an exemplary embodiment of the present invention, the process of the present invention is used to perform polymer side chain grafting via oxo-anion elaboration on a model EVA 360 using a controlled ring-opening polymerization of ethylene oxide to produce polyethylene-graft-poly(polyethylene oxide) (PE-g-PEO) copolymers under alkaline conditions was performed followed by further elaboration of the in-situ generated EVOH by reaction with 1,3 propane sultone. The process of the present invention also allows for the ability to tailor the length of the side chain to enable the further enhancement of property modification, particularly for the breathability optimization, tie-chain like toughening enhancement and blend or composite compatibility. The grafting density of the PEO side chains can be varied by the choice of the composition of the starting EVA copolymer, and the ratio of hydrophobic to hydrophilic content can be independently adjusted by the extent of ethylene oxide polymerization. The amphiphilic graft copolymers of the present invention may be used in various applications including, but not limited to, thermoplastic elastomer, films, fibers, fabrics, gels, breathable packaging materials, additive for biodegradable systems, surfactant, antistatic additives, polymer compatibilizers, phase transfer catalysts, solid polymer electrolytes, and biocompatible polymers or, incorporation into the materials listed above.

Figure 7:
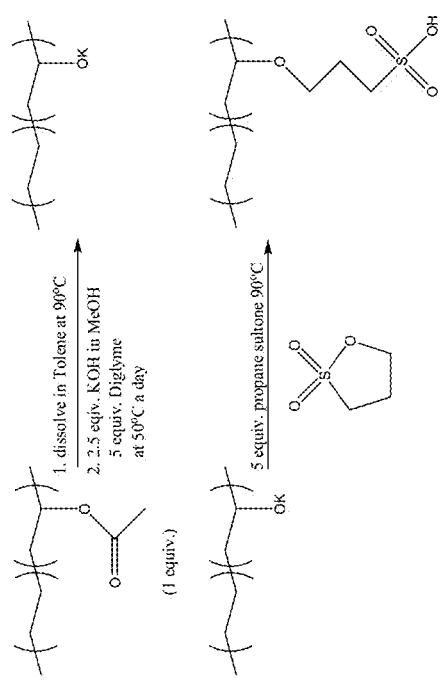
FIG. 7 shows an exemplary scheme of oxo-anion elaboration on commercially available EVA 360 resins.
Figure 8:
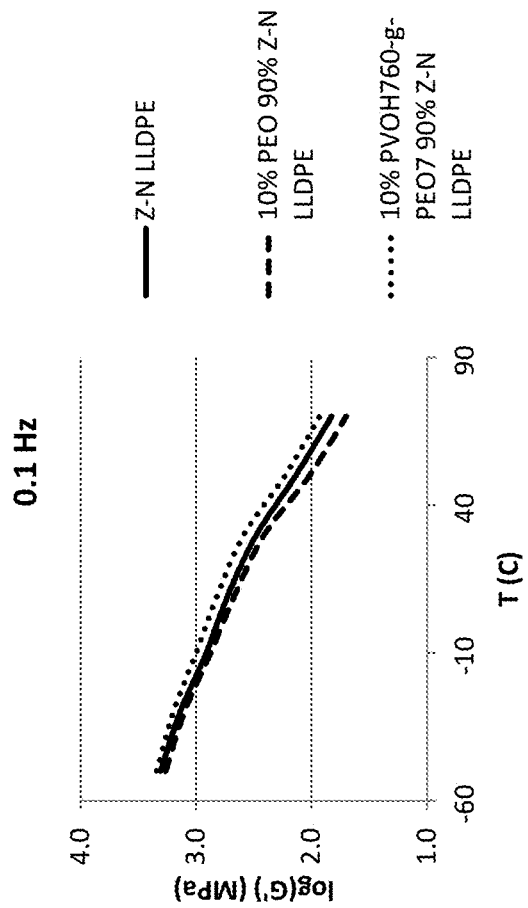
FIGS. 8-15 show a graphical representation of storage (G') and loss (G") DMA temperature sweep data by frequency of a Ziegler-Natta linear low density polyethylene; a blend of 10% PEO-90% Ziegler-Natta linear low density polyethylene; and a blend of 10% of a grafted copolymer of the present invention with 90% Ziegler-Natta linear low density polyethylene.
Figure 9:
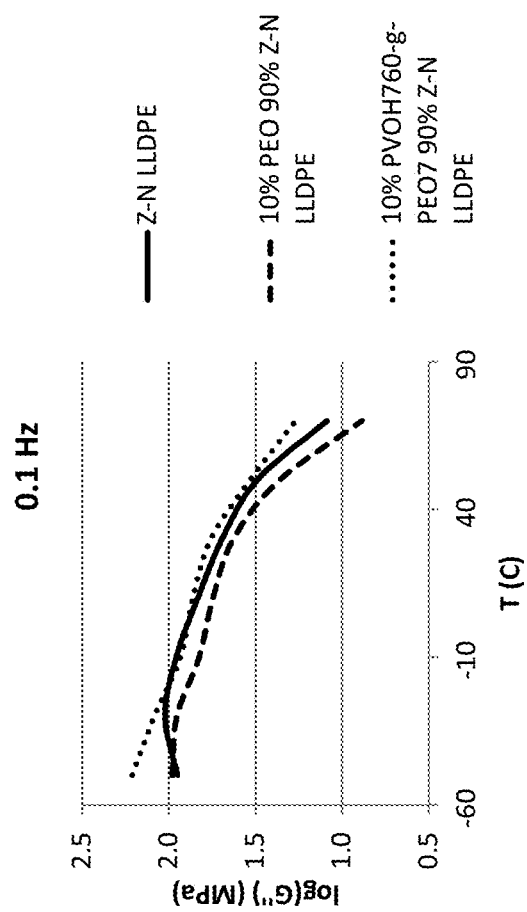
Figure 10:
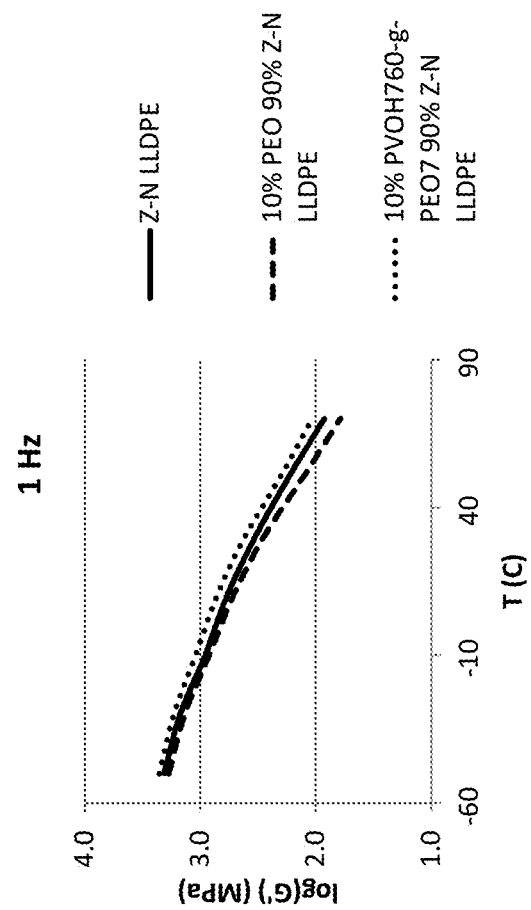
Figure 11:
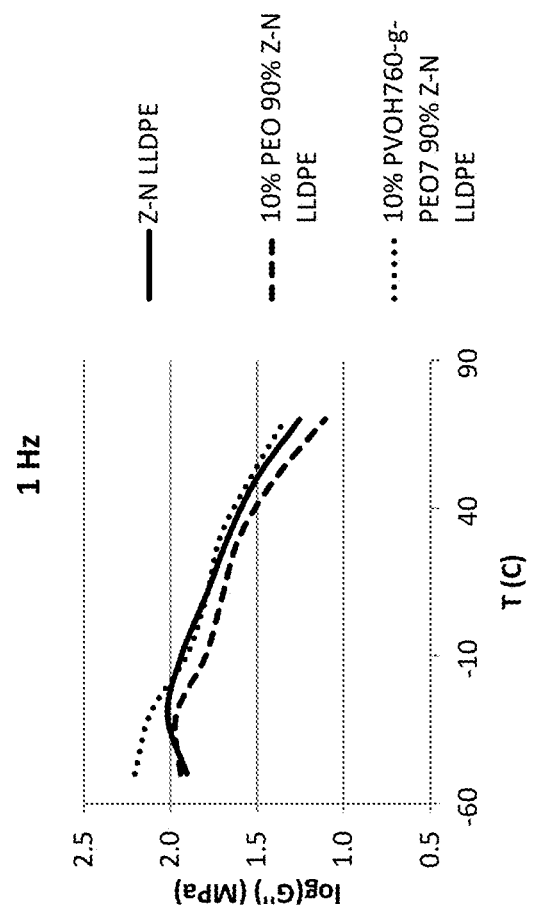
Figure 12:
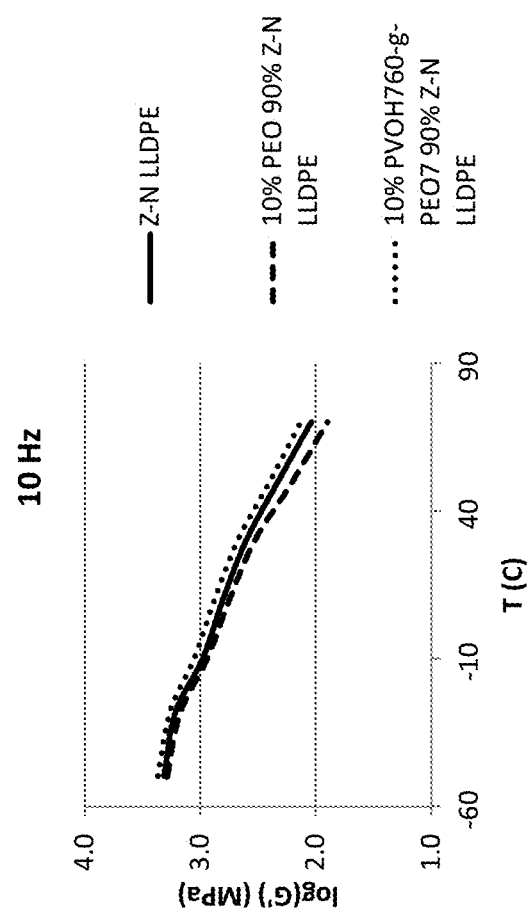
Figure 13:
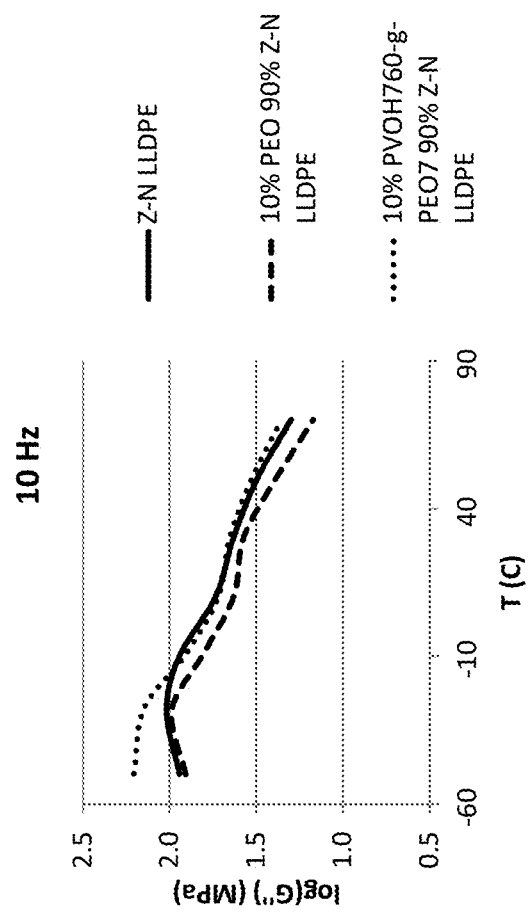
Figure 14:
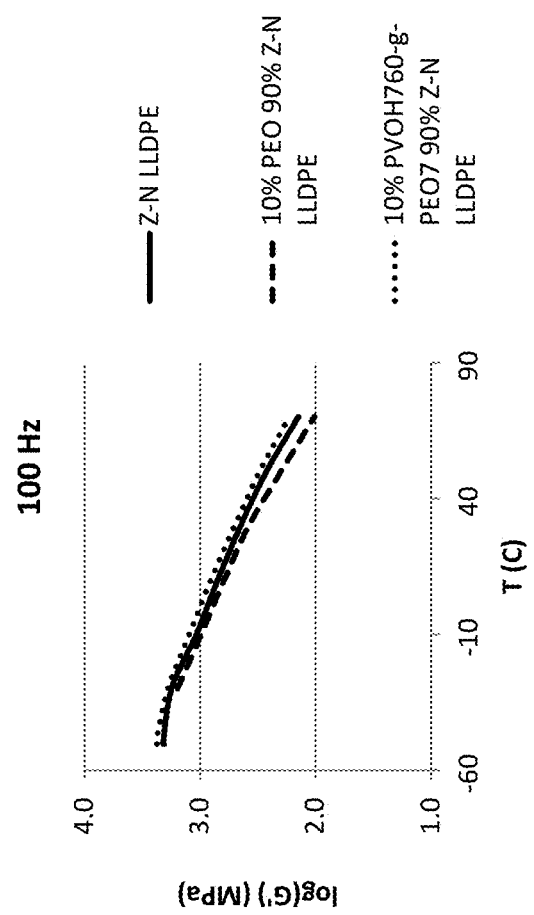
Figure 15:
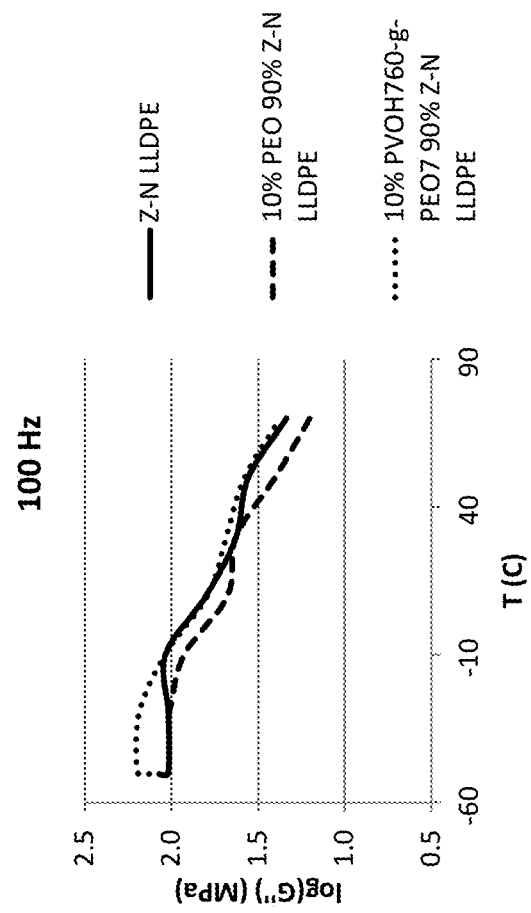

As shown in FIG. 7, 1 equivalent of EVA 360 was dissolved in toluene at 90° C. and a hydrolysis reaction was performed on EVA 360 using 2.5 equivalents of potassium methoxide in 5 equivalents of Diglyme solvent at 50° C. for a period of one day. The resultant polymeric potassium alkoxide is then used to initiate ethylene oxide ring-opening polymerization (ROP). In the second step of the process, oxo-anion polymerization is performed on (copolymers of ethylene and vinyl acetate to produce a broad range of novel polyethylene based graft-copolymers.

Applications

Polyethylene (PE) is one of the most widely used polymeric materials globally. Linear low-density polyethylene (LLDPE) in particular is used in a broad range of applications, including a component in films for packaging products and medical devices. These are polymeric materials which have been used in the medical device industry for decades and are both low cost and recyclable. The ability of the present invention to incorporate a grafted functional group along the backbone of a conventional PE would enable further enhancement of the performance and applications of PE-based materials. Because the fundamental backbone of the resultant polymeric resin would still be PE, the resultant chemically modified resin could still be readily recyclable.

Although methods of achieving breathability or porosity of packaging film may be found in the prior art, none of the known methods offer the balance of required physical attributes, microbial barrier, commercial scalability and potential price point of the commodity based resin breathable top web film as described in the present invention.

In another aspect of the present invention, the amphiphilic graft copolymer is incorporated into a blend of commodity resins to create a breathable top web film for primary packaging for medical devices that is capable of withstanding ethylene oxide sterilization. The film could provide the physical performance attributes of a polymeric film with the breathability of paper, while also maintaining microbial barrier properties. Breathable films address altitude issues experienced with non-breathable primary packages which can result in open seals due to pressure differentiation issues. Thus, breathable films may be used in air freight and in geographical areas with a higher altitude. Breathable films and membranes can be prepared from the PVOH-g-PEO copolymers, and blends thereof, by compression molding or film casting.

The PVOH-g-PEO copolymers could also be used as compatibilizers between two incompatible polymeric systems with one component being PE-based, or having an affinity for PE, and the other having an affinity for PEO, enhancing the dispersion of the secondary phase and interaction between the two phases resulting in enhanced physical performance, as well as providing improved product consistency. Other additives could be likewise be driven to the interface between the polyethylene and the secondary phase.

Two (2) novel PE-grafted polymer films were prepared and tested to determine whether the PE-grafted films could achieve permeability and microbial barrier requirements to enable the potential application as a breathable top web for primary packaging of medical devices.

The two (2) novel PE-grafted polymer films were composed of a Ziegler-Natta linear low density PE having a density of 0.92 g/cm3 (measured using ASTM D792) and a melt index of 1 g/10 minutes (measured using ASTM D1238) as follows:
  Film A: Ziegler-Natta linear low density PE (84%), PVOH760-g-PEO7 (6%), PEO (10%); and
  Film B: Ziegler-Natta linear low density PE (70%), PVOH660-g-PEO14 (5%), PEO (25%).

The two (2) PE-grafted polymer films were tested against a non-grafted film (Film C composed of Ziegler-Natta linear low density PE (55%) and PEO (45%).

The films were prepared via melt blending and were performed in a twin-screw blender (eg. Brabender Model R.E.E. 6). The blend was fed at a rotor speed of 20 rpm at 160° C. The film was prepared using a feeding sequence wherein the Ziegler-Natta linear low density PE was fed into the blender first, followed by the PVOH-g-PEO and finally commercial PEO. The rotor speed was increased to 60 rpm upon the melt of all feeding materials. The temperature was maintained at 160° C. for 10 minutes. Upon completion of batch mixing, the blends were rapidly quenched in liquid nitrogen to freeze the morphology. To prepare the films, the blends were placed between sheets of Kapton films and then placed between the heated metal platens of a compression press (Carver, Inc). The thickness of films was controlled with 0.1 mm steel foil at 150° C. and 15000 PSI for 2 minutes. The films were quenched in liquid nitrogen once left the hot plates. Porous films were obtained from the pressed blends, followed by PEO extraction with water at room temperature for 12 hours.

Upon visual examination, the PE-grafted polymer films were more transparent and homogenous in comparison to the non-grafted film (Film C composed of Ziegler-Natta linear low density PE (55%) and PEO (45%). The non-grafted film (Film C composed of Ziegler-Natta linear low density PE (55%) and PEO (45%) has distinct phases, voids and is not transparent which is a strong visual indicator of incompatibility and non-homogeneity in the non-grafted film. The visual examination of the grafted films evidences that the addition of the PVOH-g-PEO is a compatibilizer for Ziegler-Natta linear low density PE and PEO.

FIGS. 8-15 show DMA data by frequency. The temperature sweeps shows the 10% PVOH-g-PEO/90% Z-N LLDPE blend sample has a more consistent G' (storage) and G" (loss) modulus over the temperature range of at least (−50 C to 70 C) over a broad frequency range of at least 0.1 Hz to 100 Hz. With equivalent or greater moduli over at least the given temperature range. This G' and G" data also shows that the 10% PVOH-g-PEO/90% Z-N LLDPE blend sample has the least softening characteristics at elevated temperatures, >40 C. Note there is a slightly lower loss (G") modulus for the 10% PVOH-g-PEO/90% Z-N LLDPE blend sample specifically at −10 C compared to the neat Z-N LLDPE sample. This is not taken to be impactful compared to the overall trend of the blend sample as a function of temperature and frequency.

Figure 16:
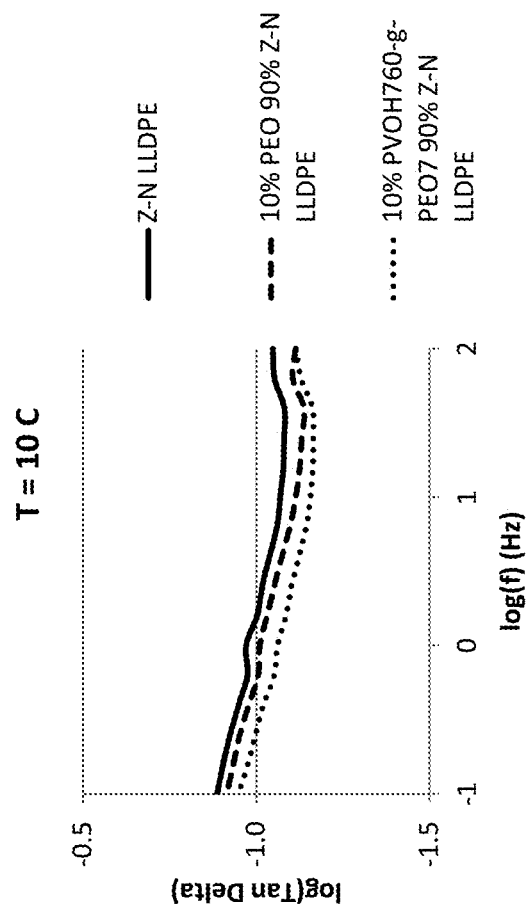
FIG. 16-18 show a graphical representation of the tan delta DMA frequency sweep data by temperature of samples of of a Ziegler-Natta linear low density polyethylene; a blend of 10% PEO-90% Ziegler-Natta linear low density polyethylene; and a blend of 10% of a grafted copolymer of the present invention with 90% Ziegler-Natta linear low density polyethylene.
Figure 17:
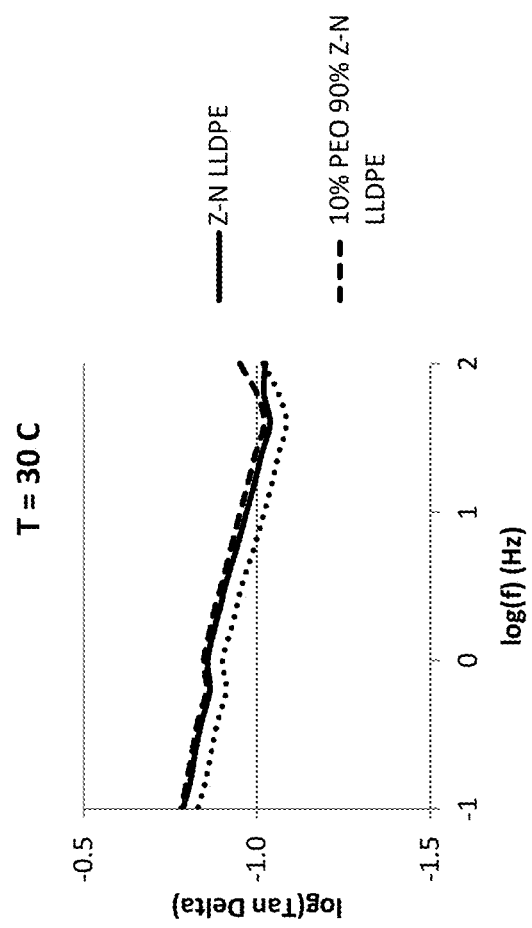
Figure 18:
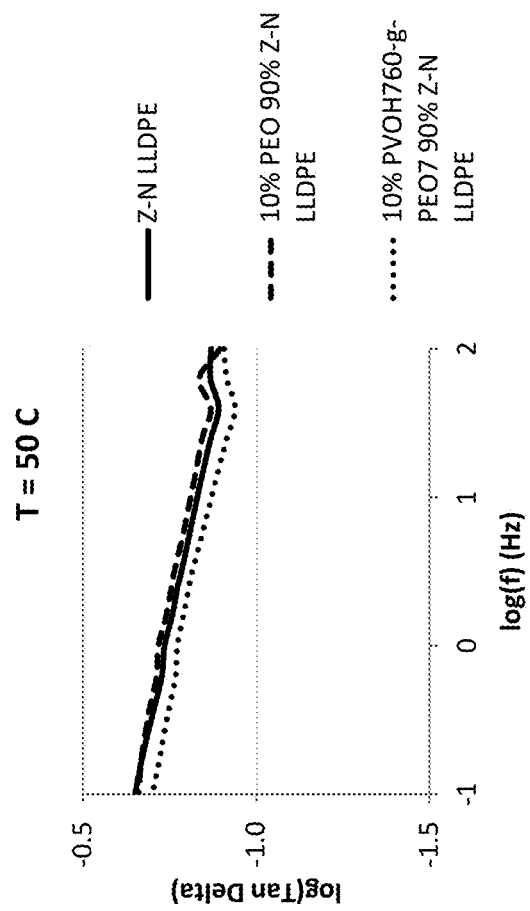

FIG. 16-18 show a graphical representation of the tan delta of samples of a Ziegler-Natta linear low density polyethylene; a blend of 10% PEO-90% Ziegler-Natta linear low density polyethylene; and a blend of 10% of a grafted copolymer of the present invention with 90% Ziegler-Natta linear low density polyethylene. The tan delta curves at 10, 30, and 50° C., for the 10% PVOH-g-PEO/90% Z-N LLDPE blend sample shows the lowest tan delta, especially at the lower frequencies <10 Hz. This shows this material will have improved shape and dimensional stability over the temperature range for commercial applications, such a medical devices, which could be EtO sterilized and/or stored in uncontrolled environments and used in tropical climates. The low frequency, 0.1 Hz, data is suggestive this material will have improved creep and compression set resistance over the temperature range commercial products could be exposed too. This is an advantaged property to maintain functional performance of products comprising of at least one component comprised of the PVOH-g-PEO polymer over the product lifetime especially if under molded in or assembly stresses.

As shown in FIG. 19, PE-grafted polymer films can be controlled to be both permeable to allow breathability while at the same time having a percentage of penetration to be less than 0.1% thus providing for a microbial barrier compared to the non-grafted film of Ziegler-Natta linear low density PE (55%) and PEO (45%) which is not a microbial barrier and is fully permeable. A film were composed of pure Ziegler-Natta linear low density PE having a density of 0.92 g/cm3 and a melt index of 1 g/10 minutes, while a microbial barrier, would not be permeable and generally do not allow air penetration as defined in the ISO 11607 std.

Controlled oxo-anion ring-opening polymerization of ethylene oxide will yield novel compositions of iPE-g-PEO. The grafting density of the PEO side chains can be varied by the choice of the composition of the starting iPE-diol copolymer. The ratio of hydrophobic to hydrophilic content can be independently adjusted by the extent of ethylene oxide polymerization. The process of the present invention provides a broad range of control over sample compositions. Molecular weight and side chain graft density will be a function of the starting grafted polyethylene, and the control over the side-chain length will be a direct function of the length of time the ROP of ethylene oxide is performed. Breathable films and membranes can be prepared from the PE-g-PEO copolymers, and blends thereof, by compression molding or film casting. Breathable membranes can be prepared from the PE-g-PEO copolymers.

The PE-g-PEO copolymers could also be used as compatibilizers between two incompatible polymeric systems with one component being PE-based, or having an affinity for PE, and the other having an affinity for PEO, enhancing the dispersion of the secondary phase and interaction between the two phases resulting in enhanced physical performance, as well as providing improved product consistency. The PE-g-PEO copolymers of the present invention may also be used as a toughening agent to increase the physical performance attributes of polyethylene, including impact, tear, or puncture resistance.

Other additives could be likewise be driven to the interface between the polyethylene and the secondary phase, such as exfoliated graphene or clay platelets for enhanced oxygen barrier properties. Oxygen scavengers could likewise be incorporated. Due to high level of dispersion and propensity for the additive to move to the blend interface, lower levels of additives would need to be incorporated for a higher level of performance and enhanced efficiency.

The top web films comprising of the present invention could provide a cost savings in specialized applications where commercially available products such as Tyvek is needed. Additionally, paper is highly subject to property degradation over time and under challenging environmental conditions, especially when subjected to Cobalt or E-Beam sterilization. These breathable films would provide a more long-term structurally stable packaging alternative. This film could be used for any application which requires controlled breathability, such a fresh food packaging applications.

The graft modified EVA-based copolymers of the present invention could also be used as a breathable flow wrap packaging material. The cost and performance of currently available flow wrap with a breathable feature, such as a paper strip, is expensive, difficult to run and slow to sterilize. The breathable film of the present invention offers a cost-effective packaging material having improved mechanical properties and anticipated higher ethylene oxide permeation rate resulting in a substantially increased sterilization throughput rate.

A top web film incorporating the amphiphilic graft copolymer of the present invention will have structural and sealant properties comparable to existing packaging film structures, while maintaining robust physical & processing properties to meet a broad spectrum of packaging lines and products to be used in a variety of environment conditions including areas of high humidity and temperature.

In another aspect of the present invention, an improved thermoplastic elastomer (TPE) is provided incorporating the amphiphilic copolymers of the present invention. The thermoplastic elastomer of the present invention may be used for injection molded applications such as medical device components including syringe stoppers, blood collection and closed-system transfer device membranes, and IV drip chambers. The thermoplastic elastomer of the present invention may also be used for extrusion applications such as IV tubing, catheter extension set tubing and catheter tubing. Additionally, for stopper applications, there is a desire to move from the conventional thermalset rubbers to an injection moldable thermoplastic elastomer which can also be reprocessed, resulting in processing efficiencies, less waste, and potential cost savings.

For syringe stoppers TPE's have been evaluated as a replacement to conventional thermoset rubbers. Due to the melt and crystallization characteristics of TPEs they can be injection molded and reprocessed, where as conventional thermoset rubber stoppers must be cut from sheets, with the unused material being disposed of as scrap. A stopper formulation must achieve the appropriate balance of compression set and elastomeric conformability. For membrane applications, current TPE based membranes are challenged to provide a desired balance of good sealability, high compression set, high wear resistance, and resistance to coring. For stopper and membrane applications, the thermoplastic elastomer of the present invention may be used in two potential approaches to achieve the desired balance of properties. As shown in FIGS. 16-18, this material will have improved creep and compression set resistance over the temperature range commercial products could be exposed as suggested by the low frequency, 0.1 Hz. By controlling the composition, frequency, and length of the grafted side chains to manipulate the crystalline structure as well as the molecular entanglement of the final TPE material and control mobility and subsequently compression set and creep. A controlled amount of cross-linking could be imparted post-injection molding to provide additional strength and avoid undesired properties related to creep and deformation, such as sticktion. In another embodiment of the present invention, the grafting architecture and frequency of polymerization along the backbone would be tailored to create a semi-crystalline backbone with an amorphous or semi-crystalline grafted side chain on the resultant graft copolymer to achieve the desired balance of properties for the stopper or membrane applications. In one or more embodiments, it is desired to have PEO side chains long enough to also crystallize to create a more complex crystalline structure. Thus, by controlling the composition, frequency, and length of the grafted side chains to manipulate the crystalline structure, as well as, the molecular entanglement of the final TPE material, allows for control of the mobility and subsequently compression set and creep. Together these molecular attributes would govern the rheological and physical properties of the final product.

For IV tubing, current TPE formulations cannot yet meet the desired performance attributes of plasticized PVC. Plasticized PVC is desired for its low set, high kink resistance, deformation recoverability, clarity, and tactile feel. An additional challenge with non-polar TPEs is the bonding of the IV tubing to connectors and other fixtures. These connections are typically done via solvent bonding.

Catheter tubing may lose some of its strength in regions of elevated temperature and humidity, thus causing difficulty in catheter stick, threading, advancing, and other catheter related complications. Non-ideal pre-insertion softening characteristics can lead to catheter complications such as excessive sticktion during insertion.

Many current TPE formulations use some type of plasticizer in their formulation and most IV tubing and extension sets are comprised of plasticized PVC. For environmental reasons, there is a desire to remove di-2-ethyl-hexylphthalate (DEHP) and other phthalate-based plasticizers from the PVC formulation, as well as, to eliminate the use of PVC entirely. An improved thermoplastic elastomer (TPE) incorporating the amphiphilic copolymers of the present invention would serve this need.

For IV tubing, one approach to address the current deficiencies of conventional TPEs would be to utilized the process of the present invention to produce a copolymer having grafted side chains to break up the crystallinity of the PE backbone and avoid the undesirable plastic deformation which can occur in semi-crystalline TPEs which results in a propensity for kinking and/or permanent set after clamping. A controlled amount of cross-linking could be imparted post-extrusion to the grafted copolymer of the present invention to provide additional strength. Polar functionality and other functional attributes could be also incorporated on the graft side chain of the copolymers of the present invention to overcome the inherent difficulty of solvent bonding TPE tubing to connectors and other fixtures.

Figure 20:
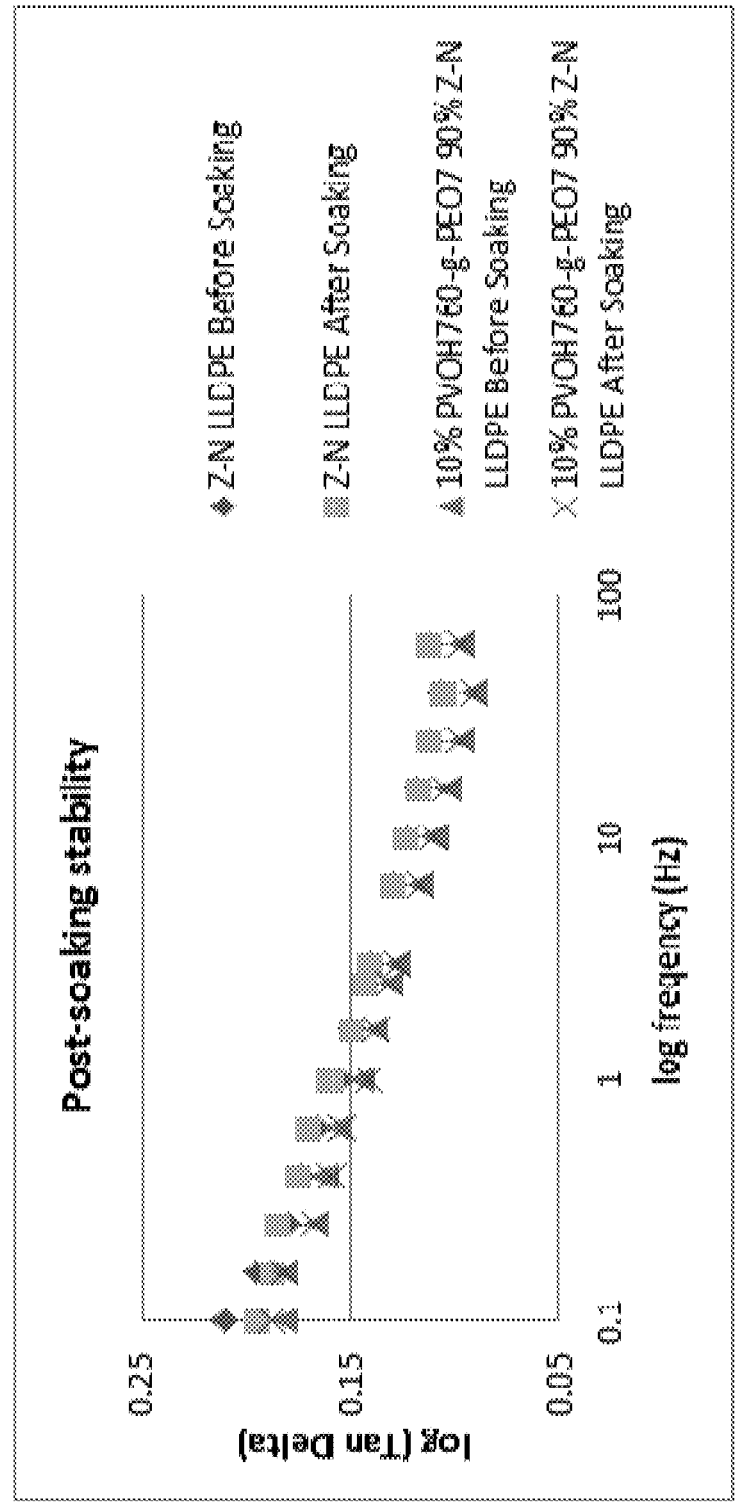
FIG. 20 shows a graphical representation of the tan delta of samples of a Ziegler-Natta linear low density polyethylene; a blend of 10% of a grafted copolymer of the present invention with 90% Ziegler-Natta linear low density polyethylene. before and after soaking.

For the catheter tubing, a climate-stable catheter tubing could be achieved through utilizing the process of the present invention. As discussed above, by controlling the composition, frequency, and length of the grafted side chains to manipulate the crystalline structure, as well as, the molecular entanglement of the final TPE material, allows for control of the mobility and subsequently compression set and creep. In one or more embodiments of the present invention, a more thermally stable, hydrophobic component would comprise the matrix of the tubing material along with a secondary phase of a hydrophilic component tailored to have a softening temperature appropriate to the internal body temperature. An optimized balance of hydrophobicity, hydrophilicity, and softening temperature of the catheter tubing material could be achieved by incorporating a hydrophilic system along the backbone of the hydrophobic PE backbone resulting in a catheter tubing which is stronger pre-insertion, has greater softening characteristics upon insertion into the body, and enabling an overall greater ability for tailoring of performance attributes. This would enable production of a catheter tubing that would be stable in high temperature and humidity conditions and climates and also reduce catheter related complications. Dynamic Mechanical Anaysis (DMA) experiments were conducted to show the stability of the grafted copolymers of the present invention. To conduct the DMA experiment, the copolymer samples were merged in reverse osmosis (RO) water at 40° C. for two hours. The samples were patted dried prior to running the DMA experiments. DMA was run at 40° C., at a frequency scan from 0.1-63 Hz. As shown in FIG. 20, 90% Ziegler-Natta linear low density PE having a density of 0.92 g/cm3 (measured using ASTM D792) and a melt index of 1 g/10 minutes (measured using ASTM D1238) and 10% PVOH-g-PEO blend sample shows stability in regards to viscoelastic properties after exposure to extreme moisture conditions (i.e. submerged in water). The tan delta curves for the 10% PVOH-g-PEO/90% Ziegler-Natta linear low density PE having a density of 0.92 g/cm3 and a melt index of 1 g/10 minutes blend sample shows the lowest tan delta, especially at the lower frequencies <10 Hz. The low frequency, 0.1 Hz, data is suggestive this material will have improved creep and compression set resistance over the temperature range commercial products could be exposed too. This is an advantaged property to maintain functional performance of products comprising of at least one component comprised of the PVOH-g-PEO polymer over the product lifetime especially if under molded in or assembly stresses. This is advantaged for performance stability in commercial applications, such a medical devices, which could be EtO sterilized and/or stored in uncontrolled environments and used in tropical climates.

As discussed, thermal analysis by differential scanning calorimetry (DSC) can be used to determine glass transitions temperature and melting points of the resultant semi-crystalline graft copolymers. Thermal analysis by DSC may be used to establish the expected dual semi-crystalline character of the resultant copolymers. As shown in Table 6, DSC scans highlight that the graft polymer may help PE crystallization in a blend system.

TABLE 6

| Samples | PEO Heat Flow Portion (J/g) | PE Heat Flow Portion (J/g) |
|---|---|---|
| Z-N LLDPE (51.33%), PVOH760-g-PEO7(3.67%), PEO (45%) | 57.58 | 64.51 |
| Z-N LLDPE (55%), PEO (45%) | 73.76 | 53.51 |

As shown in FIG. 21, the surface energy of the blend can be controlled moving from hydrophilic to hydrophobic, also the high contact angles (hydrophobic) after the PEO extraction support that the PEO was truly removed from the system.

To show self-adhesion of the grafted films, two sample batches of films were prepared as follows: Sample 1 consisted of a blend of 90% by weight of a Ziegler-Natta linear low density PE having a density of 0.92 g/cm3 (measured using ASTM D792) and a melt index of 1 g/10 minutes (measured using ASTM D1238) and 10% by weight of PEO 200 kDa. Sample 2 consisted of a blend of 90% by weight of a Ziegler-Natta linear low density PE having a density of 0.92 g/cm3 (measured using ASTM D792) and a melt index of 1 g/10 minutes (measured using ASTM D1238) and 10% by weight of grafted PVOH760-g-PEO. Each batch was 40 grams and the blends were prepared in a Brabender Model R.E.E. blender 60 rpm at 160° C. for 10 minutes. It was determined that Sample 2 has some adhesion and tack properties allowing Sample 2 to stick to itself or stick to a smooth surface for a while without need for any additional adhesive. In contrast, Sample 1 and a film of pure Ziegler-Natta linear low density PE did not show adhesion and tack properties. The sample films show that a small amount of grafted PVOH760-g-PEO (10%) can result in tackiness and self-adhesive surface properties.

Since the fundamental backbone of a TPE system incorporating the grafted copolymer of the present invention would still be PE, the resultant product is capable of being readily recyclable.

Another aspect of the present invention is the use of graft modified EVA-based copolymers as an additive for biodegradable polymeric systems such as PLA or PCL (poly (caprolactone). As an additive, these graft modified EVA-based resins would increase the thermal and mechanical properties of the biodegradable system thereby providing mechanical performance enhancement while still yielding a biodegradable and largely bioderived system.

The incorporation of an EVOH-g-PLA copolymer of the present invention into a packaging or medical device serves as a mechanical property enhancer by resulting in an increase in the modulus and elongation-to-break resulting in an overall increased toughness, including increased impact, tear, or puncture resistance.

The graft modified EVA-based copolymers of the present invention could also be used as compatibilizers between two incompatible polymeric systems with one of the components being PE-based or random ethylene copolymer PP-based materials. As compatibilizers, the graft copolymers of the present invention would serve to improve the dispersion of the secondary phase and interaction between the two phases resulting in enhanced physical performance and provide improved product consistency. The graft modified EVA-based copolymers of the present invention may also be used as a toughening agent to increase the physical performance attributes of polyethylene or random ethylene copolymer PP-based materials, including increased impact, tear, or puncture resistance. The length of the side chain of the graft modified copolymers could be tailored to optimize the toughening enhancement and strength/toughness balance characteristics for PE-based films. An optimized balance, and enhancement, of the impact and tear resistance of the films could be achieved. This could also be achieved by incorporation of the graft modified copolymers into a PE or or random ethylene copolymer PP-based film, or film layer, thus enabling down gauging of the film for packaging applications allowing for less packaging waste and potential cost savings.

Other additives could be likewise driven to the interface between the polyethylene, or random ethylene copolymer PP-based materials, and secondary phase, such as, but not limited to, exfoliated graphene or clay platelets for enhanced oxygen barrier properties. Oxygen scavengers could likewise be incorporated. Due to high level of dispersion and propensity for the additive to move to the blend interface, lower levels of additives would need to be incorporated for a higher level of performance and enhanced efficiency.

The chemistry incorporated onto the functional graft of the PE or PP backbone could be used for product surface functionalization or modification including, but not limited to, creating an anti-microbial surface; creating a surface with greater biocompatibility; anti-inflammatory; biofilm formation suppressant; self-lubricating or higher-slip surfaces; creating an anti-fouling surface; and adhesive surfaces.

Other potential applications of the graft copolymers of the present invention include, but not limited to, use as surfactants, antistatic additives, polymer compatibilizers, phase transfer catalysts, solid polymer electrolytes, and biocompatible polymers.

Grafting agents, such as polybutymethacylate, can be used for additional functionality such as an anti-proliferative, anti-inflammatory, or anti-coagulant. The graft modified EVA-based copolymers could also be used to create a drug or protein eluting coating or product. Drug elution rate may be controlled by the degree of hydrolysis of the EVA starting material. For these applications, a controlled release of the drug is desired to reduce both short and long term restenosis. If a bioactive drug is released too quickly into the body at too great of a concentration, this "bolus" can result in localized inflammation and inhibit the healing process. EVA is currently used in many biomedical applications as a drug and/or protein eluting material due to its good flexibility, thermoplastic nature, stability, and low cost.

The graft modified EVA-based copolymers can also be used in applications such as films, fibers, fabrics, blends and mixtures. The vinyl groups of the vinyl acetate may be used to create gels through controlled cross linking.

Figure 22:
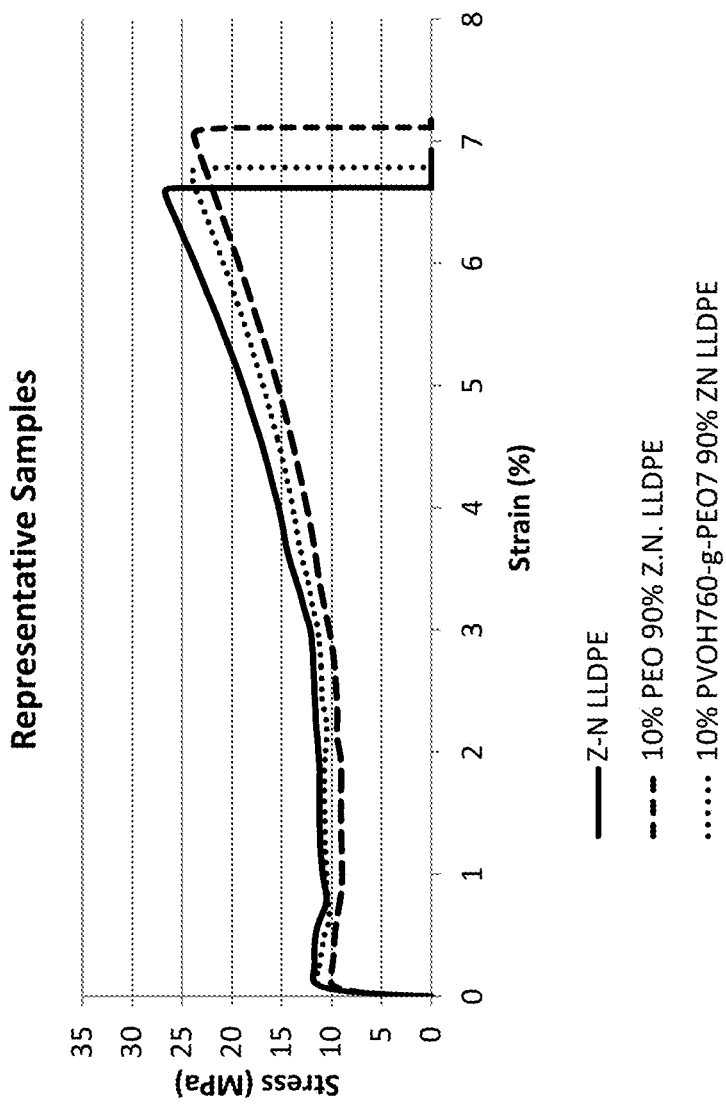
FIG. 22 shows stress strain data to prove material physical properties are maintained after grafting process of the present invention.

FIG. 22 shows stress strain data to prove material physical properties are maintained after grafting process of the present invention.

Due to the backbone linking nature of the side chain and the fact that the modification process of the present invention does not degrade the molecular weight of the starting material, the grafted materials of the present invention will have fewer extractable and leachable compared to conventional blends or other modification techniques. Therefore, the grafted copolymers of the present invention mitigate unintended interactions with infusates or excipients, and the transmission of those components to the patient thus making the grafted copolymers of the present invention ideal for medical device applications. The graft modified copolymers of the present invention are in compliance with materials of concern restrictions as listed in Prop 65 and REACH.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. An amphiphilic copolymer of the formula (I):

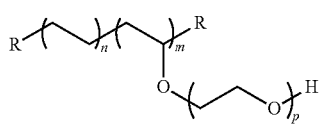

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 30 to 500 ethylene oxide units.

2. The amphiphilic copolymer of claim 1, wherein R is hydrogen.

3. The amphiphilic copolymer of claim 1, wherein the poly(ethylene oxide) groups are grafted by oxo-anion ring-opening polymerization.

4. The amphiphilic copolymer of claim 1 having a number average molecular weight (Mn) in the range about 80 to about 1000 kDa.

5. The amphiphilic copolymer of claim 1, wherein p is in the range of 30 to 250 ethylene oxide units.

6. An additive comprising the amphiphilic copolymer of claim 1.

7. A compatibilizer comprising the amphiphilic copolymer of claim 1.

8. A thermoplastic elastomer comprising the amphiphilic copolymer of claim 1.

9. A top web film comprising the amphiphilic copolymer of claim 1.

10. An amphiphilic copolymer of the formula (II):

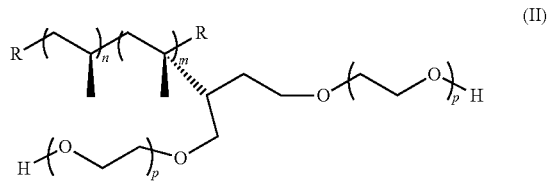

wherein R is hydrogen, alkyl, substituted alkyl, vinylic substituted alkyl, hydrocarbyl, substituted hydrocarbyl, or vinylic substituted hydrocarbyl group; the molar percentages of grafted maleic anhydride units, m, is in the range from 2 to 10 mole percent; the molar values of propylene units, n, is in the range from 98 to 90 mole percent, and p is in the range of 50 to 500 ethylene oxide units.

11. The amphiphilic copolymer of claim 10, wherein R is hydrogen.

12. The amphiphilic copolymer of claim 10, wherein the poly(ethylene oxide) groups are grafted by oxo-anion ring-opening polymerization.

13. The amphiphilic copolymer of claim 10 having a number average molecular weight (Mn) in the range about 80 to about 1000 kDa.

14. The amphiphilic copolymer of claim 10, wherein p is in the range of 50 to 250 ethylene oxide units.

15. An additive comprising the amphiphilic copolymer of claim 10.

16. A compatibilizer comprising the amphiphilic copolymer of claim 10.

17. A thermoplastic elastomer comprising the amphiphilic copolymer of claim 10.

18. A top web film comprising the amphiphilic copolymer of claim 10.

19. A component of a medical device formed from a blend comprising:
one or both of polyethylene and a thermoplastic elastomer (TPE); and
an additive comprising one or both of: a polyethylene-poly(ethylene oxide) amphiphilic graft copolymer (PE-g-PEO) and a polypropylene-poly(ethylene oxide) amphiphilic graft copolymer (PP-g-PEO);
wherein the polyethylene-poly(ethylene oxide) amphiphilic graft copolymer (PE-g-PEO) is according to Formula (I):

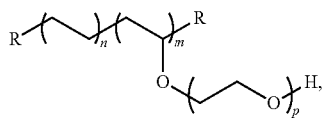
(I)

wherein R is hydrogen, alkyl, substituted alkyl, vinylic substituted alkyl, hydrocarbyl, substituted hydrocarbyl, or vinylic substituted hydrocarbyl group; the molar value of m is in the range from 2 to 40 mole percent; the molar value of n is in the range from 60 to 98 mole percent; and p is in the range from 5 to 500 ethylene oxide units;
and
wherein the polypropylene-poly(ethylene oxide) amphiphilic graft copolymer (PP-g-PEO) is according to Formula (II):

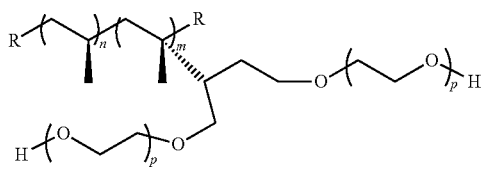
(II)

wherein R is hydrogen, alkyl, substituted alkyl, vinylic substituted alkyl, hydrocarbyl, substituted hydrocarbyl, or vinylic substituted hydrocarbyl group; m, the molar percentages of grafted maleic anhydride units, is in the range from 2 to 10 mole percent; n, the molar values of propylene units, is in the range from 98 to 90 mole percent, and p is in the range of 5 to 500 ethylene oxide units.

20. The component of a medical device of claim 19 in the form of a film or a tubing.

21. The component of a medical device of claim 20 in the form of the film, comprising the polyethylene.

22. The component of a medical device of claim 21, wherein the additive comprises the PE-g-PEO.

23. The component of a medical device of claim 22, wherein the film has a percent penetration of less than 0.1%.

24. The component of a medical device of claim 20, wherein the additive is present in the blend in an amount of about 3-10% by weight.

25. The component of a medical device of claim 24, wherein in Formula (I), p is in the range of 30 to 500 ethylene oxide units.

26. The component of a medical device of claim 24, wherein in Formula (II), p is in the range of 50 to 500 ethylene oxide units.

* * * * *

UNITED STATES PATENT AND TRADEMARK OFFICE
CERTIFICATE OF CORRECTION

PATENT NO. : 10,336,852 B2  
APPLICATION NO. : 15/484593  
DATED : July 2, 2019  
INVENTOR(S) : Theresa Hermel-Davidock et al.

Page 1 of 1

It is certified that error appears in the above-identified patent and that said Letters Patent is hereby corrected as shown below:

On the Title Page

Page 2, Column 2, item (56) under "OTHER PUBLICATIONS", insert --CHEN, et al., "Break Through in Breathable Polymers: Morphology, Properties, and Performance", Dupont, Wilimington, DE, 1-8.--.

Page 2, Column 2, item (56) under "OTHER PUBLICATIONS", insert --Pebax in Medical Applications, 2 pgs.--.

In the Specification

Column 3, Line 65, after "on the", delete "a".

Column 6, Line 19, before "a Ziegler-Natta", delete "of".

Column 6, Line 31, after "ethylene", delete ".".

Column 22, Line 28, after "PE", delete "or".

Signed and Sealed this  
Tenth Day of September, 2019

Andrei Iancu  
*Director of the United States Patent and Trademark Office*